(12) United States Patent
Beliveau et al.

(10) Patent No.: US 8,828,949 B2
(45) Date of Patent: *Sep. 9, 2014

(54) APROTININ POLYPEPTIDES FOR TRANSPORTING A COMPOUND ACROSS THE BLOOD-BRAIN BARRIER

(75) Inventors: Richard Beliveau, Verdun (CA); Michel Demeule, Beaconsfield (CA); Christian Che, Longueuil (CA); Anthony Regina, Montreal (CA)

(73) Assignee: Angiochem, Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/042,017

(22) Filed: Mar. 7, 2011

(65) Prior Publication Data

US 2011/0171128 A1  Jul. 14, 2011

Related U.S. Application Data

(63) Continuation of application No. 11/884,629, filed as application No. PCT/CA2005/001158 on Jul. 21, 2005, now Pat. No. 7,902,156.

(60) Provisional application No. 60/653,928, filed on Feb. 18, 2005.

(51) Int. Cl.
| | |
|---|---|
| A61K 38/04 | (2006.01) |
| A61K 38/16 | (2006.01) |
| A61K 38/22 | (2006.01) |
| C07K 9/00 | (2006.01) |
| G01N 33/53 | (2006.01) |
| A61K 35/30 | (2006.01) |

(52) U.S. Cl.
USPC .......... 514/21.4; 514/17.7; 514/9.7; 530/300; 977/915

(58) Field of Classification Search
None
See application file for complete search history.

(56) References Cited

U.S. PATENT DOCUMENTS

| | | | |
|---|---|---|---|
| 4,671,958 A | 6/1987 | Rodwell et al. | |
| 4,801,575 A | 1/1989 | Pardridge | |
| 4,902,505 A | 2/1990 | Pardridge et al. | |
| 4,942,184 A | 7/1990 | Haugwitz et al. | |
| 5,028,697 A | 7/1991 | Johnson et al. | |
| 5,041,424 A | 8/1991 | Saulnier et al. | |
| 5,118,668 A | 6/1992 | Auerswald et al. | |
| 5,169,933 A | 12/1992 | Anderson et al. | |
| 5,258,499 A | 11/1993 | Konigsberg et al. | |
| 5,578,451 A | 11/1996 | Nishimoto | |
| 5,627,270 A | 5/1997 | Kahne et al. | |
| RE35,524 E | 6/1997 | Saulnier et al. | |
| 5,683,694 A | 11/1997 | Bagshawe et al. | |
| 5,780,265 A | 7/1998 | Dennis et al. | |
| 5,807,980 A | 9/1998 | Lasters et al. | |
| 5,869,045 A | 2/1999 | Hellstrom et al. | |
| 5,922,754 A | 7/1999 | Burchett et al. | |
| 5,948,888 A | 9/1999 | de la Monte et al. | |
| 5,955,444 A | 9/1999 | Ingram et al. | |
| 5,962,266 A * | 10/1999 | White et al. | 435/69.2 |
| 5,981,564 A | 11/1999 | Page et al. | |
| 6,093,692 A | 7/2000 | Shen et al. | |
| 6,126,965 A | 10/2000 | Kasid et al. | |
| 6,191,290 B1 | 2/2001 | Safavy | |
| 6,245,359 B1 | 6/2001 | Milstein et al. | |
| 6,306,993 B1 | 10/2001 | Rothbard et al. | |
| 6,316,024 B1 | 11/2001 | Allen et al. | |
| 6,348,207 B1 | 2/2002 | Milstein et al. | |
| 6,376,648 B2 | 4/2002 | White et al. | |
| 6,475,481 B2 | 11/2002 | Talmadge | |
| 6,475,781 B1 | 11/2002 | Mercola et al. | |
| 6,495,513 B1 | 12/2002 | Rueger et al. | |
| 6,613,890 B2 | 9/2003 | White et al. | |
| 6,660,525 B2 | 12/2003 | Martin et al. | |
| 6,713,454 B1 | 3/2004 | Ekwuribe et al. | |
| 6,906,033 B2 | 6/2005 | White et al. | |
| 6,930,090 B2 | 8/2005 | Ekwuribe et al. | |
| 7,902,156 B2 * | 3/2011 | Beliveau et al. | 514/21.4 |
| 2003/0129186 A1 | 7/2003 | Beliveau et al. | |
| 2004/0077540 A1 | 4/2004 | Quay | |
| 2004/0146549 A1 | 7/2004 | Ben-Sasson et al. | |
| 2004/0220132 A1 | 11/2004 | Kaemmerer | |
| 2005/0042227 A1 | 2/2005 | Zankel et al. | |
| 2005/0058702 A1 | 3/2005 | Ben-Sasson et al. | |
| 2005/0100986 A1 | 5/2005 | Verma et al. | |

FOREIGN PATENT DOCUMENTS

| | | |
|---|---|---|
| CA | 2283474 | 9/1999 |
| CA | 2525236 | 1/2005 |
| DE | 19953696 | 5/2001 |

(Continued)

OTHER PUBLICATIONS

Ma et al., "Cationic Charge-Dependent Hepatic Delivery of Amidated Serum Albumin," J. Controlled Release, 102:583-594, 2005.
Marino et al., "Transcytosis of Retinol-Binding Protein Across Renal Proximal Tubule Cells After Megalin (gp 330)-Mediated Endocytosis," J. Am. Soc. Nephrol., 12:637-648, 2001.
Marino et al., "Megalin-Mediated Transcytosis of Thyroglobulin by Thyroid Cells is a Calmodulin-Dependent Process," Thyroid, 10:461-469, 2000.
Martel et al., "Transport of Apolipoproteins E and J at the Blood-Brain Barrier Relevance to Alzheimer's Disease," STP Pharma. Sciences, 7:28-36, 1997.
Mazel M et al., "Doxorubicin-Peptide Conjugates Overcome Multidrug Resistance," Anti-Cancer Drugs, 12:107-116, 2001.

(Continued)

Primary Examiner — Daniel E Kolker
Assistant Examiner — Aditi Dutt
(74) Attorney, Agent, or Firm — Duane Morris LLP; Lee Crews

(57) ABSTRACT

The invention relates to improvements in the field of drug delivery. More particularly, the invention relates to polypeptides derived from aprotinin and from aprotinin analogs as well as conjugates and pharmaceutical compositions comprising these polypeptides or conjugates. The present invention also relates to the use of these polypeptides for transporting a compound or drug across the blood-brain barrier of a mammal and in the treatment and diagnosis of neurological diseases.

37 Claims, 9 Drawing Sheets

(56) References Cited

FOREIGN PATENT DOCUMENTS

| EP | 0393431 A1 | 10/1990 |
|---|---|---|
| WO | WO87/05702 | 9/1987 |
| WO | WO96/31531 | 10/1996 |
| WO | WO96/35788 | 11/1996 |
| WO | WO96/39183 | 12/1996 |
| WO | WO96/40210 | 12/1996 |
| WO | WO97/33996 | 9/1997 |
| WO | WO97/40854 | 11/1997 |
| WO | WO00/01417 | 1/2000 |
| WO | WO00/71574 | 11/2000 |
| WO | WO01/30319 | 5/2001 |
| WO | WO02/33090 | 4/2002 |
| WO | WO03/009815 | 2/2003 |
| WO | WO2004/060403 | 7/2004 |
| WO | WO2005/002515 | 1/2005 |

OTHER PUBLICATIONS

McCarty, "Cell Biology of the Neurovascular Unit: Implications for Drug Delivery Across the Blood-Brain Barrier," Assay and Drug Development Technologies, 3:89-95, 2005.

Moestrup et al., "Evidence that Epithelial Glycoprotein 330/Megalin Mediates Uptake of Polybasic Drugs," J. Clin. Invest. 96:1404-1413, 1995.

Muratovska et al., "Conjugate for Efficient Delivery of Short Interfering RNA (siRNA) into Mammalian Cells," FEBS Letters, 558:63-68, 2004.

Ngo et al., "Computational Complexity; Protein Structure Prediction, and the Levinthal Paradox," The Protein Folding Problem and Tertiary Structure Prediction, pp. 492-495, 1994.

Orlando et al., "Identification of the Second Cluster of Ligand-Binding Repeats in Megalin as a Site for Receptor-Ligand Interactions," Proc. Natl. Acad. Sci. USA, 94:2368-2373, 1997.

Pan et al., "Efficient Transfer of Receptor-Associated Protein (RAP) Across the Blood-Brain Barrier," J. Cell Sci., 117:5071-5078, 2004.

Pardridge, "Blood-Brain Barrier Biology and Methodology," J. NeuroVirology, 5:556-569, 1999.

Pardridge, "CNS Drug Design Based on Principles of Blood-Brain Barrier Transport," J. Neurochem., 70:1781-1792, 1998.

Peri et al., "D-Glucose as a Regioselectively Addressable Scaffold for Combinatorial Chemistry on Solid Phase," J. Carbohydrate Chem., 22:57-71, 2003.

Prince et al., "Lipoprotein Receptor Binding, Cellular Uptake, and Lysosomal Delivery of Fusions Between the Receptor-associated Protein (RAP) and α-L-Iduronidase or Acid α-Glucosidase," J. Biol. Chem., 279:35037-35046, 2004.

Ramakrishnan, "The Role of P-Glycoprotein in the Blood-Brain Barrier," Einstein Quart. J. Biol. Med., 19:160-165, 2003.

Regina et al., "Differences in Multidrug Resistance Phenotype and Matrix Metalloproteinases Activity Between Endothelial Cells from Normal Brain and Glioma," J. Neurochem., 84:316-324, 2003.

Rouselle et al., "New Advances in the Transport of Doxorubicin Through the Blood-Brain Barrier by a Peptide Vector-Mediated Strategy," Mol. Pharmacol., 57:679-686, 2000.

Rudikoff et a;l., "Single Amino Acid Substitution altering antigen-binding specificity," Proc. Natl. Acad. Sci., 79:1979-1983, 1982.

Saito et al., "Drug Delivery Strategy Utilizing Conjugation Via Reversible Disulfide Linkages: Role and Site of Cellular Reducing Activities," Advanced Drug Delivery Reviews, 55:199-215, 2003.

Scherrmann, "Drug Delivery to Brain Via the Blood-Brain Barrier," Vascular Pharmacology, 38:349-354, 2002.

Schiff et al., "Taxol Stabilizes Microtubules in Mouse Fibroblast Cells," Proc. Natl. Acad. Sci. USA, 77:1561-1565,1980.

Schinkel, "P-Glycoprotein, a Gatekeeper in the Blood-Brain Barrier," Advanced Drug Delivery Reviews, 36:179-194,1999.

Seidel et al., "Effects of Trasylol on the Blood-Brain Barrier in Rats," Document R73, p. 284 XP008030270, 1974.

Shibata et al., "Clearance of Alzheimer's Amyloid-β1-40 Peptide from Brain by LDL Receptor-Related Protein-1 at the Blood-Brain Barrier," J. Clin. Invest., 106:1489-1499, 2000.

Shiiki et al., "Brain Insulin Impairs Amyloid-β(1-40) Clearance from the Brain," J. Neurosci., 24:9632-9637, 2004.

Shimura et al., "Transport Mechanism of a New Behaviorally Highly Potent Adrenocorticotropic Hormone (ACTH) Analog, Ebiratide, through the Blood-Brain Barrier," J. Pharmacol. and Exp. Therapeutics, 258:459-465, 1991.

Skolnick et al., "From Genes to Protein Structure and Function: Novel Applications of Computational Approaches in the Genomic Era," TIBTECH, 18:34-39, 2000.

Smith, "Brain Perfusion Systems for Studies of Drug Uptake and Metabolism in the Central Nervous System," Models for Assessing Drug Absorption and Metabolism, Plenum Press, New York, 1996.

Smith et al., "The Challenges of Genome Sequence Annotation or 'The Devil is in the Details,'" Nature Biotechnol., 15:1222-1223, 1997.

Steiniger et al., "Chemotherapy of Glioblastoma in Rats Using Doxorubicin-Loaded Nanoparticles," Int. J. Cancer, 109:759-767, 2004.

Takei et al., "A Small Interfering RNA Targeting Vascular Endothelial Growth Factor as Cancer Therapeutics," Cancer Res., 64:3365-3370, 2004.

Tamai et al., "Structure-Internalization Relationship for Adsorptive-Mediated Endocytosis of Basic Peptides at the Blood-Brain Barrier," J. Pharmacol. and Exp. Therapeutics, 280:410-415, 1997.

Temsamani et al., "Vector-Mediated Drug Delivery to the Brain," Expert Opin. Biol. Ther., 1:773-782, 2001.

Terasaki et al., "New Approaches to In Vitro Models of Blood-Brain Barrier Drug Transport," Drug Discovery Today, 8:944-954, 2003.

Trail et al., "Cure of Xenografted Human Carcinomas by BR96-Doxorubicin Immunoconjugates," Science 261:212-215, 1993.

Triguero et al., "Capillary Depletion Method for Quantification of Blood-Brain Barrier Transport of Circulating Peptides and Plasma Proteins," J. Neurochem., 54:1882-1888, 1990.

Uekita et al., "Membrane-Type 1 Matrix Metalloproteinase Cytoplasmic Tail-Binding Protein-1 is a New Member of the Cupin Superfamily. A Possible Multifunctional Protein Acting as an Invasion Suppressor Down-Regulated in Tumors," J. Biol. Chem., 279:12734-12743, 2004.

Uekita et al., "Cytoplasmic Tail-Dependent Internalization of Membrane-Type 1 Matrix Metalloproteinase is Important for its Invasion-Promoting Activity," J. Cell Biol., 155:1345-1356, 2001.

Veronese et al., "PEGylation, Successful Approach to Drug Delivery," Drug Discovery Today, 10:1451-1458, 2005.

Wang et al., "DNA/Dendrimer Complexes Mediate Gene Transfer into Murine Cardiac Transplants Ex Vivo," Molecular Therapy, 2:602-608, 2000.

Wells, "Additivity of Mutational Effects in Proteins," Biochemistry, 29:8509-8517, 1990.

Witt et al., "Peptide Drug Modifications to Enhance Bioavailability and Blood-Brain Barrier Permeability," Peptides, 22:2329-2343, 2001.

Xu et al., "In Vitro and In Vivo Evaluation of Actively Targetable Nanoparticles for Paclitaxel Delivery," International J. Pharmaceutics, 288:361-368, 2005.

Yepes et al., "Tissue-Type Plasminogen Activator Induces Opening of the Blood-Brain Barrier Via the LDL Receptor-Related Protein," J. Clin. Invest., 112:1533-1540, 2003.

Zhang et al., "Intravenous RNA Interference Gene Therapy Targeting the Human Epidermal Growth Factor Receptor Prolongs Survival in Intracranial Brain Cancer," Clinical Cancer Res., 10:3667-3677, 2004.

Zhang et al., "Silencing the Epidermal Growth Factor Receptor Gene with RNAi May Be Developed as a Potential Therapy for Non Small Cell Lung Cancer," Genetic Vaccines and Therapy, 3:5, 2005.

Zlokovic et al., "Glycoprotein 330/Megalin: Probable Role in Receptor-Mediated Transport of Apolipoprotein J Alone and in a Complex with Alzheimer Disease Amyloid β at the Blood-Brain and Blood-Cerebrospinal Fluid Barriers," Proc. Natl. Acad. Sci. USA, 93:4229-4234, 1996.

Arpicco et al., "New Coupling Reagents for the Preparation of Disulfide Cross-Linked Conjugates with Increased Stability," Bioconjugate Chem., 8:327-337, 1997.

(56) References Cited

OTHER PUBLICATIONS

Ballabh et al., "The Blood-brain Barrier: An Overview Structure, Regulation, and Clinical Implications," Neurobiology of Disease, 16:1-13, 2004.
Banks, "Leptin Transport Across the Blood-Brain Barrier: Implications for the Cause and Treatment of Obesity," Current Pharmaceutical Design, 7:125-133, 2001.
Bicamumpaka et al., "In Vitro Cyotoxicity of Paclitaxel-Transferrin Conjugate on H69 Cells," Oncology Reports, 5:1381-1383, 1998.
Bickel et al., "Delivery of Peptides and Proteins Through the Blood-brain Barrier," Advanced Drug Delivery Reviews, 46:247-279, 2001.
Bork et al., "Go Hunting in Sequence Databases but Watch Out for the Traps," Trends in Genetics, 12:425-427, 1996.
Bork, "Powers and Pitfalls in Sequence Analysis: The 70% Hurdle," Genome Research, 10:398-400, 2000.
Brenner, "Errors in Genome Annotation," Trends in Genetics, 15:132-133, 1999.
Castex et al., "2-Pyrrolinodoxorubicin and Its Peptide-vectorized Form Bypass Multidrug Resistance," Anticancer Drugs, 15:609-617, 2004.
Coon et al., "Solutol HS 15, Nontoxic Polyoxethylene Esters of 12-Hydroxystearic Acid, Reverses Multidrug Resistance," Cancer Res., 51:897-902, 1991.
D'Onofrio et al., "Glycomimetics as Decorating Motifs for Oligonucleotides: Solid-phase Synthesis, Stability, and Hybridization Properties of Carbopeptoid-Oligonucleotide Conjugates," Bioconjugate Chem., 16:1299-1309, 2005.
Dagenais et al., "Development of an In Situ Mouse Brain Perfusion Model and Its Application to mdr1a P-Glycoprotein-Deficient Mice," J. Cerebral Blood Flow and Metabolism, 20:381-386, 2000.
Deane et al., "LRP/Amyloid β-Peptide Interaction Mediates Differential Brain Efflux of Aβ Isoforms," Neuron, 43:333-344, 2004.
Dehouck et al., "A New Function for the LDL Receptor: Transcytosis of LDL Across the Blood-Brain Barrier," J. Cell Biol., 138:877-889, 1997.
Dehouck et al., "An Easier, Reproducible, and Mass-Production Method to Study the Blood-Brain Barrier In Vitro," J. Neurochem., 54:1798-1801, 1990.
Dehouck et al., "Drug Transfer Across the Blood-Brain Barrier: Correlation Between In Vitro and In Vivo Models," J. Neurochem., 58:1790-1797, 1992.
Demeule et al., "Isolation of Endothelial Cells from Brain, Lung, and Kidney: Expression of the Multidrug Resistance P-Glycoprotein Isoforms," Biochem. and Biophys. Res. Comm., 281:827-834, 2001.
Demeule et al., "High Transcytosis of Melanotransferrin (P97) Across the Blood-Brain Barrier," J. Neurochem., 83:924-933, 2002.
Demeule et al., "Drug Transport to the Brain: Key Roles for the Efflux Pump P-Glycoprotein in the Blood-Brain Barrier," Vascular Pharmacol., 38:339-348, 2002.
Doerks et al., "Protein Annotation: Detective Work for Function Prediction," Trends in Genetics, 14:248-250, 1998.
Dooley et al., "An All D-Amino Acid Opiod Peptide with Central Analgesic Activity from a Combinatorial Library," Science, 266:2019-2022, 1994.
Eigenbrot et al., "X-Ray Structure of Glial Cell-Derived Neurotrophic Factor at 1.9 Å Resolution and Implications for Receptor Binding," Nature Struct. Biol., 4:435-438, 1997.
Fillebeen et al., "Receptor-mediated Transcytosis of Lactoferrin through the Blood-Brain Barrier," J. Biol. Chem., 274:7011-7017, 1999.
Fromm, "P-glycoprotein: A Defense Mechanism Limiting Oral Bioavailability and CNS Accumulation of Drugs," Int. J. of Clin. Pharmacol. Therapeutics, 38:69-74, 2000.
Gabius et al., "Targeting of Neoglycoprotein-Drug Conjugates to Cultured Human Embryonal Carcinoma Cells," J. Cancer Res. Clin. Oncol., 113:126-130, 1987.
Garsky et al., "The Sythesis of a Prodrug of Doxorubicin Designed to Provide Reduced Systemic Toxicity and Greater Target Efficacy," J. Med. Chem., 44:4216-4224, 2001.
Gelmon, "The Taxoids: Paclitaxel and Docetaxel," Lancet, 344:1267-1272, 1994.
Gewirtz, "A Critical Evaluation of the Mechanisms of Action Proposed for the Antitumor Effects of the Anthracycline Antibiotics Adriamycin and Daunorubicin," Biochem. Pharmacol., 57:727-741, 1999.
Gottschalk et al., "Protein Self-Association in Solution: The Bovine Pancreatic Trypsin Inhibitor Decamer," Biophys. J., 84:3941-3958, 2003.
Grabb et al., "Neoplastic and Pharmacological Influence on the Permeability of an In Vitro Blood-Brain Barrier," J. Neurosurg., 82:1053-1058, 1995.
Grimm et al., "Ten Year Biochemical Outcomes Following 125-iodine Monotherapy for Early Stage Prostate Cancer," I. J. Radiation Oncol., 48:146-147, 2000.
Guillot et al., "Angiotensin Peptide Regulation of Bovine Brain Microvessel Endothelial Cell Monolayer Permeability," J. Cardiovasc. Pharmacol., 18:212-218, 1991.
Gumbleton et al., "Progress and Limitations in the Use of In Vitro Cell Cultures to Serve as Permeability Screen for the Blood-Brain Barrier," J. Pharmaceutical Sci., 90:1681-1698, 2001.
Hawkins et al., "The Blood-Brain Barrier/Neurovascular Unit in Health and Disease," Pharmacol. Rev., 57:173-185, 2005.
Huang et al., "Targeting Delivery of Paclitaxel Into Tumor Cells Via Somatostatin Receptor Endocystosis," Chemistry and Biology, 7:453-461, 2000.
Hussain et al., "The Mammalian Low-Density Lipoprotein Receptor Family," Annu. Rev. Nutr., 19:141-172, 1999.
Karyekar et al., "Zonula Occludens Toxin Increases the Permeability of Molecular Weight Markers and Chemotherapeutic Agents Across the Bovine Brain Microvessel Endothelial Cells," J. Pharmaceutical Sci., 92:414-423, 2003.
Kiernan et al., "Fluorescent-Labelled Aprotinin: A New Reagent for the Histochemical Detection of Acid Mucosubstances," Histochemie, 34:77-84, 1973.
Kilic et al., "Intravenous TAT-GDNF Is Protective After Focal Cerebral Ischemia in Mice," Stroke, 34:1304-1310, 2003.
Kirsch et al., "Anti-Angiogenic Treatment Strategies for Malignant Brain Tumors," J. Neuro-Oncol., 50:149-163, 2000.
Kobayashi et al., "The Protease Inhibitor Bikunin, a Novel Anti-Metastatic Agent," Biol. Chem., 384:749-754, 2003.
Koo et al., "Differential Expression of Amyloid Precursor Protein mRNAs in Cases of Alzheimer's Disease and in Aged Nonhuman Primates," Neuron, 2:97-104, 1990.
Kounnas et al., "LDL Receptor-Related Protein, a Multifunctional ApoE Receptor, Binds Secreted β-Amyloid Precursor Protein and Mediates Its Degradation," Cell, 82:331-340, 1995.
Koziara et al., "In Situ Blood-Brain Barrier Transport of Nanoparticles," Pharmaceut. Res., 20:1772-1778, 2003.
Kreuter et al., "Apolipoprotein-mediated Transport of Nanoparticle-bound Drugs Across the Blood-Brain Barrier," J. Drug Targeting, 10:317-325, 2002.
Kreuter et al., "Direct Evidence that Polysorbate-80-Coated Poly(Butylcyanoacrylate) Nanoparticles Deliver Drugs to the CNS via Specific Mechanisms Requiring Prior Binding of Drug to the Nanoparticles," Pharmaceut. Res., 20:409-416, 2003.
Laccabue et al., "A Novel Taxane Active Against an Orthotopically Growing Human Glioma Xenograft," Cancer, 92:3085-3092, 2001.
Lai et al., "The Critical Component to Establish In Vitro BBB Model: Pericyte," Brain Research Reviews, 50:258-265, 2005.
Larionova et al., "Carbohydrate-Containing Derivatives of the Trypsin-Kallikrein Inhibitor Aprotinin from Bovine Organs," Biol. Chem. Hoppe-Seyler, 366:743-748, 1985.
Lewis et al., "Maleimidocysteineamido-DOTA Derivatives: New Reagents for Radiometal Chelate Conjugation to Antibody Sulfhydryl Groups Undergo pH-Dependent Cleavage Reactions," Bioconjugate Chem., 9:72-86, 1998.

* cited by examiner

| Peptide | Amino acid sequence | Charge |
|---|---|---|
| Angiopep | TFFYGGCRGKRNNFKTEEY | +2 |
| # 67 | TFFYGGCRGKRNNFKTEEY-amide | +2 |
| # 76 | TFFYGGCRGKRNNFKTKEY-amide | +3 |
| # 91 | RFKYGGCLGNKNNYLRLKY-amide | +5 |
| # 5 | TFFYGGCRAKRNNFKRAKY-amide | +6 |

Charge + : lysine (K), arginine (R)
Charge − : glutamic acid (E), aspartic acid (D)

Fig. 9

APROTININ POLYPEPTIDES FOR TRANSPORTING A COMPOUND ACROSS THE BLOOD-BRAIN BARRIER

CROSS-REFERENCE TO RELATED APPLICATIONS

This application is a continuation of U.S. patent application Ser. No. 11/884,629, which is the U.S. national stage filing of International Application No. PCT/CA2005/001158, filed Jul. 21, 2005, which claims the benefit of U.S. Provisional Application No. 60/653,928, filed Feb. 18, 2005.

FIELD OF THE INVENTION

The present invention relates to improvements in the field of drug delivery. More particularly, the invention relates to polypeptides, conjugates and pharmaceutical compositions comprising the polypeptides or conjugates of the present invention. The present invention also relates to the use of these polypeptides and conjugates for transporting a compound or drug across the blood-brain barrier of a mammal and in the treatment and diagnosis of neurological diseases.

BACKGROUND OF THE INVENTION

In the development of a new therapy for brain pathologies, the blood-brain barrier (BBB) is considered as a major obstacle for the potential use of drugs for treating disorders of the central nervous system (CNS). The global market for CNS drugs was $33 billion in 1998, which was roughly half that of global market for cardiovascular drugs, even though in the United States, nearly twice as many people suffer from CNS disorders as from cardiovascular diseases. The reason for this lopsidedness is that more than 98% of all potential CNS drugs do not cross the blood-brain barrier. In addition, more than 99% of worldwide CNS drug development is devoted solely to CNS drug discovery, and less than 1% is directed to CNS drug delivery. This ratio could explain why no efficient treatment is currently available for the major neurological diseases such as brain tumors, Alzheimer's and stroke.

The brain is shielded against potentially toxic substances by the presence of two barrier systems: the blood-brain barrier (BBB) and the blood-cerebrospinal fluid barrier (BCSFB). The BBB is considered to be the major route for the uptake of serum ligands since its surface area is approximately 5000-fold greater than that of BCSFB. The brain endothelium, which constitutes the BBB, represents the major obstacle for the use of potential drugs against many disorders of the CNS.

As a general rule, only lipophilic molecules smaller than about 500 Daltons may pass across the BBB, i.e., from blood to brain. However, the size of many drugs that show promising results in animal studies for treating CNS disorders is considerably bigger. Thus, peptide and protein therapeutics are generally excluded from transport from blood to brain, owing to the negligible permeability of the brain capillary endothelial wall to these drugs. Brain capillary endothelial cells (BCECs) are closely sealed by tight junctions, possess few fenestrae and few endocytic vesicles as compared to capillaries of other organs. BCECs are surrounded by extracellular matrix, astrocytes, pericytes and microglial cells. The close association of endothelial cells with the astrocyte foot processes and the basement membrane of capillaries are important for the development and maintenance of the BBB properties that permit tight control of blood-brain exchange.

International publication WO2004/060403 discloses an invention made by the inventors relating to molecules for transporting a drug across the blood brain barrier. Otherwise, to date, there is no efficient drug delivery approach available for the brain. Methods under investigation for peptide and protein drug delivery to the brain may be divided in three principal strategies. Firstly, invasive procedures include the direct intraventricular administration of drugs by means of surgery, and the temporary disruption of the BBB via intra-carotid infusion of hyperosmolar solutions. Secondly, the pharmacologically-based strategy consists in facilitating the passage through the BBB by increasing the lipid solubility of peptides or proteins. Thirdly, physiologic-based strategies exploit the various carrier mechanisms at the BBB, which have been characterized in the recent years. In this approach, drugs are attached to a protein vector that performs like receptors-targeted delivery vehicle on the BBB. This approach is highly specific and presents high efficacy with an extreme flexibility for clinical indications with unlimited targets. The latter approach has been, and is still, investigated by the inventors, who came up with the molecules described in the afore-mentioned publication and those of the present invention.

U.S. Pat. No. 5,807,980 describes Bovine Pancreatic Trypsin Inhibitor (aprotinin)-derived inhibitors as well as a method for their preparation and therapeutic use. These peptides are used for the treatment of a condition characterized by an abnormal appearance or amount of tissue factor and/or factor VIIIa such as abnormal thrombosis.

U.S. Pat. No. 5,780,265 describes serine protease inhibitors that are capable of inhibiting plasma kallikrein.

U.S. Pat. No. 5,118,668 describes Bovine Pancreatic Trypsin Inhibitor variants.

It would be highly desirable to be provided with improved molecules that can act as carriers or vectors for transporting a compound or drug across the BBB of an individual.

SUMMARY OF THE INVENTION

One aim of the present invention is to provide an improvement in the field of drug delivery.

Another aim of the present invention is to provide a non-invasive and flexible method and carrier for transporting a compound or drug across the blood-brain barrier of an individual.

The present application discloses new molecules which may be capable, for example, of transporting desirable compounds across the blood-brain barrier.

In a first aspect the present invention provides a biologically active polypeptide which may be able to cross (i.e., crossing) a cell layer mimicking (which mimics) a mammalian blood brain barrier in an in vitro assay, the polypeptide may be selected, for example, from the group of
  aprotinin (SEQ ID NO.:98),
  an aprotinin analogue
  an aprotinin fragment which may comprise (or may consist essentially of) the amino acid sequence defined in SEQ ID NO.:1,
  a biologically active analogue of SEQ ID NO.:1,
  a biologically active fragment of SEQ ID NO.:1, and;
  a biologically active fragment of a SEQ ID NO.:1 analogue.

In a second aspect the present invention provides, a biologically active polypeptide which may be able to cross (i.e., crossing) a cell layer mimicking (which mimics) a mammalian blood brain barrier in an in vitro assay, the polypeptide may be selected, for example, from the group of;

an aprotinin fragment which may comprise the amino acid sequence defined in SEQ ID NO.:1,
a biologically active analogue of SEQ ID NO.:1,
a biologically active fragment of SEQ ID NO.:1 and;
a biologically active fragment of a SEQ ID NO.:1 analogue.

In accordance with the present invention the aprotinin fragment may consist of the sequence defined in SEQ ID NO.:1. Further in accordance with the present invention, the aprotinin fragment may comprise SEQ ID NO.1 and may have a length of from about 19 amino acids to about 54 amino acids, e.g., from 10 to 50 amino acids in length, from 10 to 30 amino acids in length etc.

In accordance with the present invention, the biologically active analogue of SEQ ID NO.:1, may have a length of from about 19 amino acids to about 54 amino acids (e.g., including for example 21 to 23, 25 to 34, 36 to 50 and 52 to 54), or of from about 19 amino acids to about 50 amino acids, or from about 19 amino acids to about 34 amino acids (e.g., 19, 20, 21, 22, 23, 25, 26, 27, 28, 29, 30, 31, 32, 33, 34), of from about 19 amino acids to about 23 amino acids or of about 19, 20, 21, 22, 23, 24, 35, 51, amino acids.

A biologically active fragment of a polypeptide (e.g., of 19 amino acids) described herein may include for example a polypeptide of from about 7, 8, 9 or 10 to 18 amino acids. Therefore, in accordance with the present invention, a biologically active fragment of SEQ ID NO.:1 or of a SEQ ID NO.:1 analogue may have a length of from about 7 to about 18 amino acids or from about 10 about 18.

U.S. Pat. No. 5,807,980 describes a polypeptide that is identified herein as SEQ ID NO.:102.

U.S. Pat. No. 5,780,265 describes a polypeptide that is identified herein as SEQ ID NO.:103.

The aprotinin amino acid sequence (SEQ ID NO.:98), the Angiopep-1 amino acid sequence (SEQ ID NO.:67), as well as some sequences of biologically active analogs may be found for example in international application no. PCT/CA2004/000011 published on Jul. 22, 2004 in under international publication no. WO2004/060403. Additionally, international publication No. WO04/060403 describes a polypeptide which is identified herein as SEQ ID NO.: 104.

U.S. Pat. No. 5,118,668 describes a polypeptide that has the sequence illustrated herein as SEQ ID NO.:105.

Examples of aprotinin analogs may be found by performing a protein "blast" (for example, using the program available through the website for Genebank) of the synthetic aprotinin sequence (or a portion thereof) disclosed in international Application No. PCT/CA2004/000011. Exemplary aprotinin analogs may be found, for example, under Accession Nos. CAA37967 (GI:58005) and 1405218C (GI:3604747).

In a further aspect the present invention provides a biologically active polypeptide which may be able to cross (i.e., crossing) a cell layer mimicking (which mimics) a mammalian blood brain barrier in an in vitro assay, the polypeptide may be selected, for example, from the group of;
an aprotinin fragment of from 19 to 54 (e.g., 19-50) amino acid long, which may comprise SEQ ID NO.:1,
an aprotinin fragment consisting of SEQ ID NO.:1,
a biologically active analogue of SEQ ID NO.:1 of from about 19 to 50 amino acids long, and;
a biologically active fragment of SEQ ID NO.:1 (of from 10 to 18 amino acids) or biologically active fragment of a SEQ ID NO.:1 analogue (of from about 10 to 18 amino acids).

In accordance with the present invention there is provided a biologically active analogue of SEQ ID NO.:1 which may be selected, for example, from the group consisting of
a SEQ ID NO.:1 analogue which may comprise at least 35% identity with the amino acid sequence of SEQ ID NO.:1,
a SEQ ID NO.:1 analogue which may comprise at least 40% identity with the amino acid sequence of SEQ ID NO.:1,
a SEQ ID NO.:1 analogue which may comprise at least 50° A) identity with the amino acid sequence of SEQ ID NO.:1,
a SEQ ID NO.:1 analogue which may comprise at least 60% identity with the amino acid sequence of SEQ ID NO.:1,
a SEQ ID NO.:1 analogue which may comprise at least 70% identity with the amino acid sequence of SEQ ID NO.:1,
a SEQ ID NO.:1 analogue which may comprise at least 80% identity with the amino acid sequence of SEQ ID NO.:1,
a SEQ ID NO.:1 analogue which may comprise at least 90% identity with the amino acid sequence of SEQ ID NO.:1 and;
a SEQ ID NO.:1 analogue which may comprise at least 95% (i.e., 96%, 97%, 98%, 99% and 100%) identity with the amino acid sequence of SEQ ID NO.:1.

For example, the biologically active analogue of SEQ ID NO.:1 may comprise an amino acid sequence selected from the group consisting of an amino acid sequence defined in any one of SEQ ID NO.:2 to SEQ ID NO.: 62, SEQ ID NO.: 68 to SEQ ID NO.: 93, and SEQ ID NO.:97 as well as 99, 100 and 101. When the polypeptide of the present invention comprises, for example, SEQ ID NO.:99, 100 or 101, the polypeptide may have an amino acid sequence of from about 10 to 50 amino acids, e.g., from 10 to 30 amino acids in length.

Further in accordance with the present invention, the biologically active analogue of SEQ ID NO.:1 may comprise the amino acid sequence defined in SEQ ID NO.:67 (i.e., polypeptide no. 67 which is an amidated version of SEQ ID NO.:67 (Angiopep-1)).

The polypeptides of the present invention may be amidated, i.e., may have an amidated amino acid sequence. For example, the polypeptide of SEQ ID NO.:67 may be amidated (polypeptide no. 67).

Portion of the present invention may relate to the polypeptides defined herein with the exception of polypeptides defined in SEQ ID NO.: 102, 103, 104 and 105, while other portion of the invention may include these peptides. For example and without limitation, conjugates comprising these peptides as well as their use for treating a neurological disease (e.g., brain tumor), method of treatment of a neurological disease (e.g., brain tumor), pharmaceutical composition for treating a neurological disease, etc. are encompassed by the present invention.

In yet a further aspect the present invention provides a biologically active polypeptide which may be able to cross (i.e., crossing) a cell layer mimicking (which mimics) a mammalian blood brain barrier in an in vitro assay, the polypeptide may be selected, for example, from the group of;
an aprotinin fragment of from 19 to 54 (e.g., 19-50) amino acid long, which may comprise SEQ ID NO.:1,
an aprotinin fragment consisting of SEQ ID NO.:1,
a biologically active analogue of SEQ ID NO.:1 of from about 19 to 50 amino acids long, provided that said analogue does not comprise SEQ ID NO.: 102, 103, 104 or 105 and provided that when said analogue consists of SEQ ID NO.:67 said analogue is amidated,
a biologically active fragment of SEQ ID NO.:1 of from 10 to 18 amino acids, and;
a biologically active fragment of a SEQ ID NO.:1 analogue of from about 10 to 18 amino acids.

Further in accordance with the present invention, the biologically active fragment of SEQ ID NO.:1 or the biologically active fragment of a SEQ ID NO.:1 analogue may comprise at least 9 or at least 10 (consecutive or contiguous) amino acids of SEQ ID NO.1 or of the SEQ ID NO.:1 analogue.

The polypeptides of the present invention may have an amino acid sequence which may comprise of from between 1 to 12 amino acid substitutions (i.e., SEQ ID NO.:91). For example, the amino acid substitution may be from between 1 to 10 amino acid substitutions, or from 1 to 5 amino acid substitutions. In accordance with the present invention, the amino acid substitution may be a non-conservative amino acid substitution or a conservative amino acid substitution.

For example, when a polypeptide of the present invention comprises amino acids which are identical to those of SEQ ID NO.:1 and other amino acids which are not identical (non-identical), those which are non-identical may be a conservative amino acid substitution. The comparison of identical and non-identical amino acids may be performed by looking at a corresponding location.

Examples of SEQ ID NO.:1 analogue which may have at least 35% identity includes for example, a polypeptide comprising (consisting of) the amino acid sequence defined in SEQ ID NO.:91 (about 36.8% identity, i.e., 7 amino acid out of 19 amino acids of SEQ ID NO.:91 are identical to SEQ ID NO.:1), a polypeptide comprising (consisting of) the amino acid sequence defined in SEQ ID NO.:98 (about 68.4% identity, i.e., 13 amino acid out of 19 amino acids are identical to SEQ ID NO.:1), a polypeptide comprising (consisting of) the amino acid sequence defined in SEQ ID NO.:67 (about 73.7% identity, i.e., 14 amino acid out of 19 amino acids are identical to SEQ ID NO.:1), a polypeptide comprising (consisting of) the amino acid sequence defined in SEQ ID NO.: 76 (about 73.7% identity, i.e., 14 amino acid out of 19 amino acids are identical to SEQ ID NO.:1) and a polypeptide comprising (consisting of) the amino acid sequence defined in SEQ ID NO.:5 (about 79% identity, i.e., 15 amino acid out of 19 amino acids are identical to SEQ ID NO.:1).

Examples of SEQ ID NO.:1 analogue which may have at least 60% identity includes for example, a polypeptide comprising (consisting of) the amino acid sequence defined in SEQ ID NO.:98 (about 68.4% identity, i.e., 13 amino acid out of 19 amino acids are identical to SEQ ID NO.:1), a polypeptide comprising (consisting of) the amino acid sequence defined in SEQ ID NO.:67 (about 73.7% identity, i.e., 14 amino acid out of 19 amino acids are identical to SEQ ID NO.:1), a polypeptide comprising (consisting of) the amino acid sequence defined in SEQ ID NO.: 76 (about 73.7% identity, i.e., 14 amino acid out of 19 amino acids are identical to SEQ ID NO.:1) and a polypeptide comprising (consisting of) the amino acid sequence defined in SEQ ID NO.:5 (about 79% identity, i.e., 15 amino acid out of 19 amino acids are identical to SEQ ID NO.:1).

Examples of SEQ ID NO.:1 analogue which may have at least 70% identity includes for example, a polypeptide comprising (consisting of) the amino acid sequence defined in SEQ ID NO.:67 (about 73.7% identity, i.e., 14 amino acid out of 19 amino acids are identical to SEQ ID NO.:1), SEQ ID NO.: 76 (about 73.7% identity, i.e., 14 amino acid out of 19 amino acids are identical to SEQ ID NO.:1), SEQ ID NO.:5 (about 79% identity, i.e., 15 amino acid out of 19 amino acids are identical to SEQ ID NO.:1).

In accordance, with the present invention, the carrier may more particularly be selected from the group consisting of peptide Nos. 5, 67, 76, 91 and peptide 97 (i.e., SEQ ID NO.:5, 67, 76, 91 and 97 (Angiopep-2)). The carrier may be used, for example, for transporting an agent attached thereto across a blood-brain barrier. In accordance with the present invention, the carrier may be able to cross the blood-brain barrier after attachment to the agent and may therefore be able to transport the agent across the blood-brain barrier.

In accordance with the present invention, the polypeptides may be in an isolated form or in a substantially purified form.

More particularly, the present invention provides a carrier for transporting an agent attached thereto across a blood-brain barrier, wherein the carrier may be able to cross the blood-brain barrier after attachment to the agent and thereby transport the agent across the blood-brain barrier. The carrier may comprise at least one polypeptide of the present invention (provided that when said polypeptide or carrier consist of SEQ ID NO.:67, said polypeptide is modified by a group e.g., amidated). For example, the carrier may be selected from a class of molecules related to aprotinin.

The transporting activity which is effected by the carrier does not affect blood-brain barrier integrity. The transporting of an agent may result, for example, in the delivery of the agent to the central nervous system (CNS) of an individual.

It is to be understood herein that the polypeptides of the present invention may be synthesized chemically (e.g., solid phase synthesis) or may be produced by recombinant DNA technology. Codons which encode specific amino acids are well known in the art and is discuss, for example, in Biochemistry (third edition; 1988, Lubert Stryer, Stanford University, W.H. Freeman and Company, New-York). A nucleotide sequence encoding a carrier of the present invention is therefore encompassed herein. More particularly, nucleotide sequences (deoxyribonucleotides or ribonucleotides or derivatives thereof) encoding a polypeptide selected from the group consisting of any one of SEQ ID NO.:1 to 97, are encompassed by the present invention. An exemplary nucleotide sequence encoding an aprotinin analogue is illustrated in SEQ ID NO.:106 and may be found in Gene Bank under accession no. X04666. This sequence encodes an aprotinin analogue having a lysine at position 16 (with reference to the amino acid sequence encoded by SEQ ID NO.:106) instead of a valine as found in SEQ ID NO.:98. A mutation in the nucleotide sequence of SEQ ID NO.:106 may be introduced by methods known in the art to change the produce the peptide of SEQ ID NO.:98 having a valine in position 16. Techniques known in the art may be used to introduce further mutations in the nucleotide sequence to encode analogues of the present invention. Fragments may be obtained from this nucleotide sequence by enzymatic digestion or polymerase chain reaction, etc. Alternatively, a desired nucleotide sequence may be synthesized chemically by methods known in the art.

In a further aspect, the present invention relates to a conjugate which may comprise a carrier selected from the group consisting of any one of the polypeptide of the present invention, and an agent selected from the group consisting, for example, of a drug (e.g., a small molecule drug, e.g., an antibiotic), a medicine, a detectable label, a protein (e.g., an enzyme), protein-based compound (e.g., a protein complex comprising one or polypeptide chain) and a polypeptide (peptide). The agent may be more particularly, a molecule which is active at the level of the central nervous system. The agent may be any agent for treating or detecting a neurological disease.

In accordance with the present invention the carrier which is part of conjugate may be selected, for example, from the group of;
   an aprotinin fragment of from 10 to 54 (e.g., 19-50) amino acid long, which may comprise SEQ ID NO.:1,
   an aprotinin fragment consisting of SEQ ID NO.:1,
   a biologically active analogue of SEQ ID NO.:1 (e.g., of from about 19 to 50 amino acids long), provided that when said analogue consists of SEQ ID NO.:67 said analogue is amidated,
   a biologically active fragment of SEQ ID NO.:1 of from 10 to 18 amino acids, and;
   biologically active fragment of a SEQ ID NO.:1 analogue of from about 10 to 18 amino acids.

In accordance with the present invention, the agent may have a maximum molecular weight of about 160,000 Daltons.

Further in accordance with the present invention, the transporting activity may be effected by receptor-mediated transcytosis or adsorptive-mediated transcytosis. The agent may be one able to be transported by such mechanism.

Further in accordance with the present invention, the conjugate may be in the form of a fusion protein which may have a first moiety consisting essentially of the carrier of the present invention and a second moiety consisting essentially of a protein or protein-based agent.

Exemplary neurological diseases which may be treated or detected by the carrier and/or conjugate is a disease selected, for example, from the group consisting of a brain tumor, a brain metastasis, schizophrenia, epilepsy, Alzheimer's disease, Parkinson's disease, Huntington's disease, stroke and blood-brain barrier related malfunctions (e.g., obesity).

In accordance with the present invention, the blood-brain barrier related malfunction is obesity. Also in accordance with the present invention, the agent which may be conjugated with the carrier of the present invention may be a leptin. A conjugate comprising a leptin and a carrier may be used, for example, in the treatment of obesity.

In accordance with the present invention, the detectable label may be a radioimaging agent. Example of a label which may be conjugated with the carrier of the present invention and which is encompassed herein includes, for example and without limitation, an isotope, a fluorescent label (e.g., rhodamine), a reporter molecule (e.g., biotin), etc. Other examples of detectable labels include, for example, a green fluorescent protein, biotin, a histag protein and β-galactosidase.

Examples of proteins or protein-based compounds that may be conjugated with the carrier of the present invention and which are encompassed herein include, without limitation, an antibody, an antibody fragment (e.g., an antibody binding fragment such as an Fv fragment, an F(ab')$_2$ fragment, an Fab fragment, and the like), and a peptidic- or protein-based drug (e.g., a positive pharmacological modulator (agonist) or an pharmacological inhibitor (antagonist)). Other examples of agents that are encompassed herein include cellular toxins (e.g., monomethyl auristatin E (MMAE), bacterial endotoxins and exotoxins, diphtheria toxins, botulinum toxins, tetanus toxins, pertussis toxins, staphylococcus enterotoxins, toxic shock syndrome toxin TSST-1, adenylate cyclase toxin, shiga toxin, cholera enterotoxin, and others) and anti-angiogenic compounds (endostatin, catechins, nutraceuticals, chemokine IP-10, inhibitors of matrix metalloproteinase (MMPIs), anastellin, vitronectin, antithrombin, tyrosine kinase inhibitors, VEGF inhibitors, antibodies against receptors, Herceptin® (trastuzumab), Avastin® (bevacizumab) and Vectibix® (panitumumab) and others).

Also in accordance with the present invention, the agent may be a small molecule drug such as an anticancer drug (e.g., for treating a brain tumor). An anticancer drug encompassed by the present invention may include, for example, a drug having a group allowing it's conjugation to the carrier of the present invention. Examples of anticancer drug includes, for example, without limitation, a drug which may be selected from the group consisting of paclitaxel (Taxol), vinblastine, vincristine, etoposide, doxorubicin, cyclophosphamide, taxotere, melphalan, chlorambucil, and any combination.

More particularly, the conjugate of the present invention may comprise the formula R-L-M or pharmaceutically acceptable salts thereof, wherein R is a class of molecules related to aprotinin (e.g., aprotinin, an aprotinin fragment, Angiopep-1, Angiopep-2, or analogs, derivatives or fragments thereof). For example, R may be a carrier selected from a class of molecules related to aprotinin that are able to cross the blood-brain barrier after attachment to L-M and thereby transport M across the blood-brain barrier. L may be a linker or a bond (chemical bond). M may be an agent selected from the group consisting of a drug (e.g., a small molecule drug), a medicine, a (detectable) label, a protein or protein-based compound (e.g., an antibody, or an antibody fragment), an antibiotic, an anti-cancer agent, an anti-angiogenic compound and a polypeptide or any molecule active at the level of the central nervous system. It is to be understood that the formula R-L-M is not intended to restrict the components to a specific order or specific ratio. As exemplified herein, M may be found in several ratios over R.

For example, conjugates of formula R-L-M or a pharmaceutically acceptable salt thereof, may be used for transporting M across a blood-brain barrier, where R may be for example, a carrier selected from the group consisting of peptide Nos: 5, 67, 76, 91 and 97 as described in herein. The carrier may be able to cross the blood-brain barrier after attachment to L-M and may therefore transport M across the blood-brain barrier.

In accordance with the present invention, M may be an agent useful for treating or diagnosing a neurological disease.

It is to be understood herein that when more than one carrier conjugation site are available or present, more than one drug or drug molecule may be conjugated to the carrier of the present invention. Therefore, the conjugate may comprise one or more drug molecules. The conjugate may be active by itself, i.e., the drug may be active even when associated with the carrier. Also in accordance with the present invention, the compound may or may not be released from the carrier i.e., generally after transport across the blood-brain barrier. The compound may therefore be releasable from the conjugate (or from the carrier) and may become active thereafter. More particularly, the agent may be releasable from the carrier after transport across the blood-brain barrier.

In accordance with another embodiment of the present invention, there is provided a conjugate for transporting an agent across a blood-brain barrier, the conjugate may comprise: (a) a carrier; and (b) an agent attached to the carrier, wherein the conjugate is able to cross the blood-brain barrier and thereby transport the agent across the blood-brain barrier.

In a further aspect, the present invention relates to the use of a carrier or a conjugate of the present invention for transporting an agent across a blood brain barrier of a mammal in need thereof.

In yet a further aspect, the present invention relates to the use of a class of molecules related to aprotinin for transporting a compound attached thereto across the blood-brain barrier of a patient.

In an additional aspect, the present invention relates to the use of a carrier or a conjugate as described herein for the diagnosis of a neurological disease or a central nervous system disease. For example, the carrier or conjugate may be used for the in vivo detection of a neurological disease.

The carrier may be selected, for example, from the group of (biologically active);
aprotinin (SEQ ID NO.:98),
an aprotinin fragment which may comprise the amino acid sequence defined in SEQ ID NO.:1,
an aprotinin fragment consisting of SEQ ID NO.:1,
a biologically active analogue of SEQ ID NO.:1, and;
a biologically active fragment of SEQ ID NO.:1 or biologically active fragment of a SEQ ID NO.:1 analogue.

More particularly, the carrier may be selected, for example, from the group of (biologically active);
an aprotinin fragment which may comprise the amino acid sequence defined in SEQ ID NO.:1,
an aprotinin fragment consisting of SEQ ID NO.:1,
a biologically active analogue of SEQ ID NO.:1, and;
a biologically active fragment of SEQ ID NO.:1 or biologically active fragment of a SEQ ID NO.:1 analogue.

In accordance with the present invention, when that analogue consists of SEQ ID NO.:67, said analogue is amidated.

Even more particularly, the carrier may be selected, for example, from the group of;
an aprotinin fragment of from 10 to 54 (e.g., 19-50) amino acid long, which may comprise SEQ ID NO.:1,
an aprotinin fragment consisting of SEQ ID NO.:1,
a biologically active analogue of SEQ ID NO.:1 (e.g., of from about 19 to 50 amino acids long), provided that when said analogue consists of SEQ ID NO.:67, said analogue is amidated,
a biologically active fragment of SEQ ID NO.:1 of from 10 to 18 amino acids, and;
a biologically active fragment of a SEQ ID NO.:1 analogue of from about 10 to 18 amino acids.

In another aspect, the present invention relates to the use of a class of molecules related to aprotinin in the manufacture of a medicament.

According to the present invention, there is provided the use of a class of molecules related to aprotinin in the manufacture of a medicament for treating a neurological disease, or for treating a central nervous system disorder.

In yet another aspect, the present invention relate to the use of a carrier or conjugate described herein, in the manufacture of a medicament for treating a brain disease (a brain-associated disease) or neurological disease, for the diagnosis of a brain disease or neurological disease or for transporting an agent across the blood-brain barrier In an additional aspect, the present invention relates to the use of a carrier or conjugate of the present invention for treating a mammal having, for example, a neurological disease or for the diagnosis of a neurological disease in a mammal in need thereof.

In accordance with the present invention, neurological disease encompassed by the present invention includes, for example and without limitation, a brain tumor, a brain metastasis, schizophrenia, epilepsy, Alzheimer's disease, Parkinson's disease, Huntington's disease, stroke and blood-brain barrier related malfunctions.

In a further aspect, the present invention relates to a method for transporting an agent across the blood-brain barrier of a mammal (human, animal), which may comprise the step of administering to the mammal a compound comprising the agent attached to a class of molecules related to aprotinin.

In yet a further aspect, the present invention provides a method for treating a neurological disease of a patient comprising administering to the patient a medicament comprising a class of molecules related to aprotinin, and a compound adapted to treat the disease, the compound being attached to the class of molecules related to aprotinin.

In an additional aspect, there is provided a method for treating a central nervous system disorder of a patient comprising administering to the patient a medicament comprising a class of molecules related to aprotinin, and a compound adapted to treat the disease, the compound being attached to the aprotinin.

In yet an additional aspect there is provided a method for transporting an agent across a blood-brain barrier, which comprises the step of administering to an individual a pharmaceutical composition of the present Invention.

The present invention also relates, in a further aspect to a method for treating a mammal (e.g., a patient) in need thereof (e.g., a patient having a neurological disease). The method may comprise administering a carrier, a conjugate and/or a pharmaceutical composition of the present invention to the mammal.

The present invention additionally relates to a method for (of) diagnosing (i.e., a diagnostic method) a neurological disease in a mammal (e.g., a patient) in need thereof. The method may comprise administering a carrier, a conjugate and/or a pharmaceutical composition of the present invention to the mammal (human individual, patient, animal).

In accordance with the present invention, the administration may be performed intra-arterially, intra-nasally, intra-peritoneally, intravenously, intramuscularly, subcutaneously, transdermally or per os.

In accordance with the present invention, the pharmaceutical composition may be administered to the mammal in a therapeutically effective amount.

A mammal in need (individual in need) may be, for example, a mammal that has or is at risk of having a neurological disease, a central nervous system disease, brain cancer, a brain metastasis, etc.

In an additional aspect, the present invention relates to a pharmaceutical composition which may comprise, for example;
a carrier (which may be selected from the group consisting of any of the polypeptide described herein) or conjugate of the present invention; and
a pharmaceutically acceptable carrier, e.g., a pharmaceutically acceptable excipient.

In accordance with the present invention, the pharmaceutical composition may be used, for example, for the treatment of a neurological disease.

Further in accordance with the present invention, the pharmaceutical composition may be used, for example, for the diagnosis of a neurological disease.

Also in accordance with the present invention, the pharmaceutical composition may be used for example, for transporting an agent across a blood-brain barrier.

Also in accordance with the present invention, the pharmaceutical composition may be used for example, for the delivery of an agent to the CNS of an individual.

Further in accordance with the present invention, the pharmaceutical composition may be used for example, for treating a central nervous system disorder of a mammal in need thereof.

In accordance with the present invention, pharmaceutical composition may be used for delivery of an agent to the CNS of an individual It is to be understood herein that a pharmaceutically acceptable salts of a carrier (polypeptide) or of a conjugate is encompassed by the present invention.

The composition (pharmaceutical composition) may thus comprise a medicament manufactured as defined herein in association with a pharmaceutically acceptable excipient.

For the purpose of the present invention the following terms are defined below.

The term "carrier" or "vector" is intended to mean a compound or molecule such as a polypeptide that is able to transport a compound. For example, transport may occur across the blood-brain barrier. The carrier may be attached to (co-valently or not) or conjugated to another compound or agent and thereby may be able to transport the other compound or agent across the blood-brain barrier. For example, the carrier may bind to receptors present on brain endothelial cells and thereby be transported across the blood-brain barrier by transcytosis. The carrier may be a molecule for which high levels of transendothelial transport may be obtained, without affecting the blood-brain barrier integrity. The carrier may be, but is not limited to, a protein, a peptide or a peptidomimetic and may be naturally occurring or produced by chemical synthesis or recombinant genetic technology (genetic engineering).

The term "conjugate" is intended to mean a combination of a carrier and another compound or agent. The conjugation may be chemical in nature, such as via a linker, or genetic in nature for example by recombinant genetic technology, such as in a fusion protein with for example a reporter molecule (e.g. green fluorescent protein, β-galactosidase, Histag, etc.).

The expression "small molecule drug" is intended to mean a drug having a molecular weight of 1000 g/mol or less.

The terms "treatment", "treating" and the like are intended to mean obtaining a desired pharmacologic and/or physiologic effect, e.g., inhibition of cancer cell growth, death of a cancer cell or amelioration of a neurological disease or condition. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing a disease or condition (e.g., preventing cancer) from occurring in an individual who may be predisposed to the disease but has not yet been diagnosed as having it; (b) inhibiting a disease, (e.g., arresting its development); or (c) relieving a disease (e.g., reducing symptoms associated with a disease). "Treatment" as used herein covers any administration of a pharmaceutical agent or compound to an individual to treat, cure, alleviate, improve, diminish or inhibit a condition in the individual, including, without limitation, administering a carrier-agent conjugate to an individual.

The term "cancer" is intended to mean any cellular malignancy whose unique trait is the loss of normal controls which results in unregulated growth, lack of differentiation and ability to invade local tissues and metastasize. Cancer can develop in any tissue of any organ. More specifically, cancer is intended to include, without limitation, cancer of the brain.

The term "administering" and "administration" is intended to mean a mode of delivery including, without limitation, intra-arterially, intra-nasally, intra-peritoneally, intravenously, intramuscularly, sub-cutaneously, transdermally or per os. A daily dosage can be divided into one, two or more doses in a suitable form to be administered at one, two or more times throughout a time period.

The term "therapeutically effective" or "effective amount" is intended to mean an amount of a compound sufficient to substantially improve some symptom associated with a disease or a medical condition. For example, in the treatment of cancer or a mental condition or neurological or CNS disease, an agent or compound which decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

The carrier and conjugates of the present invention may be used in combination with either conventional methods of treatment and/or therapy or may be used separately from conventional methods of treatment and/or therapy.

When the conjugates of this invention are administered in combination therapies with other agents, they may be administered sequentially or concurrently to an individual. Alternatively, pharmaceutical compositions according to the present invention may be comprised of a combination of a carrier-agent conjugate of the present invention in association with a pharmaceutically acceptable excipient, as described herein, and another therapeutic or prophylactic agent known in the art.

Pharmaceutically acceptable acid addition salts may be prepared by methods known and used in the art and are encompassed by the present invention.

Biologically active polypeptides of the present invention encompass functional derivatives. The term "functional derivative" is intended to mean a "chemical derivative", "fragment", or "variant" biologically active sequence or portion of a carrier or agent or conjugate and a salt thereof of the present invention. A carrier functional derivative may be able to be attached to or conjugated to another compound or agent and cross the blood-brain barrier and thereby be able to transport the other compound or agent across the blood-brain barrier.

The term "chemical derivative" is intended to mean a carrier, an agent, or a conjugate of the present invention, which contains additional chemical moieties not a part of the carrier, agent or carrier-agent conjugate. Covalent modifications are included within the scope of this invention. A chemical derivative may be conveniently prepared by direct chemical synthesis, using methods well known in the art. Such modifications may be, for example, introduced into a protein or peptide carrier, agent or carrier-agent conjugate by reacting targeted amino acid residues with an organic derivatizing agent that is capable of reacting with selected side chains or terminal residues. A carrier chemical derivative is able to cross the blood-brain barrier and be attached to or conjugated to another compound or agent and thereby be able to transport the other compound or agent across the blood-brain barrier. In a preferred embodiment, very high levels of transendothelial transport across the blood-brain barrier are obtained without any effects on the blood-brain barrier integrity.

The term "agent" is intended to mean without distinction an antibody, a drug (such as a medicinal drug) or a compound such as a therapeutic agent or compound, a marker, a tracer or an imaging compound.

The term "therapeutic agent" or "agent" is intended to mean an agent and/or medicine and/or drug used to treat the symptoms of a disease, physical or mental condition, injury or infection and includes, but is not limited to, antibiotics, anti-cancer agents, anti-angiogenic agents and molecules active at the level of the central nervous system Paclitaxel, for example, can be administered intravenously to treat brain cancer.

The term "condition" is intended to mean any situation causing pain, discomfort, sickness, disease or disability (mental or physical) to or in an individual, including neurological disease, injury, infection, or chronic or acute pain. Neurological diseases which can be treated with the present invention include, but are not limited to, brain tumors, brain metastases, schizophrenia, epilepsy, Alzheimer's disease, Parkinson's disease, Huntington's disease and stroke.

As used herein, "pharmaceutical composition" means therapeutically effective amounts of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

An "analogue" is to be understood herein as a polypeptide originating from an original sequence or from a portion of an original sequence that includes one or more modifications. For example, one or more modifications in the amino acid sequence (e.g., an amino acid addition, deletion, insertion, substitution etc.), one or more modifications in the backbone or side-chain of one or more amino acids, or an addition of a group or another molecule to one or more amino acids (side-chains or backbone). An "analogue" is therefore understood herein as a molecule having a biological activity and chemical structure (or a portion of its structure) similar to that of a polypeptide described herein. An analog comprises a polypeptide that may have, for example, one or more amino acid insertions either at one or both of the ends of the polypeptide and/or inside the amino acid sequence of the polypeptide.

An "analogue" may have sequence similarity and/or sequence identity with that of an original sequence or a portion of an original sequence and may also have a modification of its structure as discussed herein. The degree of similarity between two sequences is based upon the percentage of identity (identical amino acids) and of conservative substitution(s).

Similarity or identity may be compared, for example, over a region of 2, 3, 4, 5, 10, 19, or 20 amino acids or more (and any number therebetween). Identity may include amino acids that are identical to the original peptide and that may occupy the same or a similar position when compared to the original polypeptide. An analogue that has, for example, 50% identity with an original polypeptide may include, for example, an analogue comprising 50% of the amino acid sequence of the original polypeptide. Other percentages can be similarly determined. It is to be understood that gaps may be found between the amino acids of analogues that are identical or similar to amino acids of the original peptide. The gaps may include no amino acids or one or more amino acids that are not identical or similar to the original peptide. Biologically active analogues of the carriers (polypeptides) of the present invention are encompassed herewith.

Percent identity may be determined, for example, with the algorithm GAP, BESTFIT, or FASTA in the Wisconsin Genetics Software Package Release 7.0, using default gap weights.

For example an analogue may comprise or have 50% identity with an original amino acid sequence and a portion of the remaining amino acid which occupies a similar position may be for example a non-conservative or conservative amino acid substitution.

Therefore, analogues of the present invention comprise those that may have at least 90% sequence similarity with an original sequence or a portion of an original sequence. An "analogue" may have, for example, at least 35%, 50%, 60%, 70%, 80%, 90% or 95% (96%, 97%, 98%, 99% and 100%) sequence similarity with an original sequence or a portion of an original sequence. An "analogue" may also have, for example, at least 35%, 50%, 60%, 70%, 80%, 90% or 95% (96%, 97%, 98%, 99% and 100%) sequence similarity to an original sequence with a combination of one or more modifications in a backbone or side-chain of an amino acid or an addition of a group or another molecule, etc. Exemplary amino acids that are intended to be similar (a conservative amino acid) to others are known in the art and include, for example, those listed in Table 1.

Analogues of the present invention also comprise those that may have at least 35%, 50%, 60%, 70%, 80%, 90% or 95% (96%, 97%, 98%, 99% and 100%) sequence identity with an original sequence or a portion of an original sequence. Also, an "analogue" may have, for example, 35%, 50%, 60%, 70%, 80%, 90% or 95% (sequence) identity to an original sequence (i.e., an analogue that is at least 35%, 50%, 60%, 70%, 80%, 90% or 95% identical to an original peptide) with a combination of one or more modifications in a backbone or side-chain of an amino acid, or an addition of a group or another molecule, etc.

A "fragment" is to be understood herein as a polypeptide originating from a portion of an original or parent sequence or from an analogue of said parent sequence. Fragments encompass polypeptides having truncations of one or more amino acids, wherein the truncation may originate from the amino terminus (N-terminus), carboxy terminus (C-terminus), or from the interior of the protein. A fragment may comprise the same sequence as the corresponding portion of the original sequence. Biologically active fragments of the carrier (polypeptide) described herein are encompassed by the present invention.

Thus, biologically active polypeptides in the form of the original polypeptides, fragments (modified or not), analogues (modified or not), derivatives (modified or not), homologues, (modified or not) of the carrier described herein are encompassed by the present invention.

Therefore, any polypeptide having a modification compared to an original polypeptide which does not destroy significantly a desired biological activity is encompassed herein. It is well known in the art, that a number of modifications may be made to the polypeptides of the present invention without deleteriously affecting their biological activity. These modifications may, on the other hand, keep or increase the biological activity of the original polypeptide or may optimize one or more of the particularity (e.g. stability, bioavailability, etc.) of the polypeptides of the present invention which, in some instance might be needed or desirable. Polypeptides of the present invention comprises for example, those containing amino acid sequences modified either by natural processes, such as posttranslational processing, or by chemical modification techniques which are known in the art. Modifications may occur anywhere in a polypeptide including the polypeptide backbone, the amino acid side-chains and the amino- or carboxy-terminus. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications comprise for example, without limitation, pegylation, acetylation, acylation, addition of acetomidomethyl (Acm) group, ADP-ribosylation, alkylation, amidation, biotinylation, carbamoylation, carboxyethylation, esterification, covalent attachment to fiavin, covalent attachment to a heme moiety, covalent attachment of a nucleotide or nucleotide derivative, covalent attachment of drug, covalent attachment of a marker (e.g., fluorescent, radioactive, etc.), covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination, etc. It is to be understood herein that more than one modification to the polypeptides described herein are encompassed by the present invention to the extent that the biological activity is similar to the original (parent) polypeptide.

As discussed above, polypeptide modification may comprise, for example, amino acid insertion (i.e., addition), deletion and substitution (i.e., replacement), either conservative or non-conservative (e.g., D-amino acids, desamino acids) in the polypeptide sequence where such changes do not substantially alter the overall biological activity of the polypeptide.

Examples of substitutions may be those that are conservative (i.e., wherein a residue is replaced by another of the same general type or group) or, when wanted, non-conservative (i.e., wherein a residue is replaced by an amino acid of another type). In addition, a non-naturally occurring amino acid may substitute for a naturally occurring amino acid (i.e., the substitution can be a non-naturally occurring conservative amino acid substitution or a non-naturally occurring non-conservative amino acid substitution).

As is understood, naturally occurring amino acids may be sub-classified as acidic, basic, neutral and polar, or neutral and non-polar. Furthermore, three of the encoded amino acids are aromatic. It may be of use that encoded polypeptides differing from the determined polypeptide of the present invention contain substituted codons for amino acids, which are from the same type or group as that of the amino acid be replaced. Thus, in some cases, the basic amino acids Lys, Arg and His may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable.

It should be further noted that if the polypeptides are made synthetically, substitutions by amino acids that are not naturally encoded by DNA (non-naturally occurring or unnatural amino acids) may also be made.

A non-naturally occurring amino acid is to be understood herein as an amino acid which is not naturally produced or found in a mammal. A non-naturally occurring amino acid comprises a D-amino acid, an amino acid having an acetylaminomethyl group attached to a sulfur atom of a cysteine, a pegylated amino acid, etc. The inclusion of a non-naturally occurring amino acid in a defined polypeptide sequence will therefore generate a derivative of the original polypeptide. Non-naturally occurring amino acids (residues) include also the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, norleucine, etc. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

It is known in the art that analogues may be generated by substitutional mutagenesis and retain the biological activity of the polypeptides of the present invention. These analogues have at least one amino acid residue in the protein molecule removed and a different residue inserted in its place. Examples of substitutions identified as "conservative substitutions" are shown in Table 1. If such substitutions result in a change not desired, then other type of substitutions, denominated "exemplary substitutions" in Table 1, or as further described herein in reference to amino acid classes, are introduced and the products screened.

In some cases it may be of interest to modify the biological activity of a polypeptide by amino acid substitution, insertion, or deletion. For example, modification of a polypeptide may result in an increase in the polypeptide's biological activity, may modulate its toxicity, may result in changes in bioavailability or in stability, or may modulate its immunological activity or immunological identity. Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile), Histidine (His), Tryptophan (Trp), Tyrosine (Tyr), Phenylalanine (Phe),
(2) neutral hydrophilic: Cysteine (Cys), Serine (Ser), Threonine (Thr)
(3) acidic/negatively charged: Aspartic acid (Asp), Glutamic acid (Glu)
(4) basic: Asparagine (Asn), Glutamine (Gln), Histidine (His), Lysine (Lys), Arginine (Arg)
(5) residues that influence chain orientation: Glycine (Gly), Proline (Pro);
(6) aromatic: Tryptophan (Trp), Tyrosine (Tyr), Phenylalanine (Phe), Histidine (His),
(7) polar: Ser, Thr, Asn, Gln
(8) basic positively charged: Arg, Lys, His, and;
(9) charged: Asp, Glu, Arg, Lys, His Non-conservative substitutions will entail exchanging a member of one of these classes for another. A conservative substitution will entail exchanging a member of one of these groups for another member of these groups. Alternatively other conservative amino acid substitutions are listed in Table 1.

TABLE 1 amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

A biologically active analog may be, for example, an analogue having at least one (i.e., non-conservative or conservative) amino acid substitution in the original sequence. A biologically active analog may also be for example, an analog having an insertion of one or more amino acids.

Other exemplary analogs includes for example:
A SEQ ID NO.1 analog which may have the formula I: $X_1$-SEQ ID NO.: 1-$X_2$
An Angiopep-1 analog which may have the formula II: $X_1$-Angiopep-1-$X_2$ and
An Angiopep-2 analog may have the formula III: $X_1$-Angiopep-2-$X_2$ $X_1$ and $X_2$ may independently be an amino acid sequence of from between 0 to about 100 (e.g., from between 0 to about 30 to 50) amino acids. $X_1$ and $X_2$ may be derived from consecutive amino acids of aprotinin or aprotinin analogs (homologous amino acid sequence) or may be any other amino acid sequence (heterologous amino acid sequence). A compound of either formula I, II or III may also comprises an amino acid substitution, deletion or insertion within the amino acid sequence of Angiopep-1, Angiopep-2 or SEQ ID NO.1. The analog however would preferably be biologically active as determined by one of the assays described herein or by any similar or equivalent assays.

A biologically active polypeptide (e.g., carrier) may be identified by using one of the assays or methods described herein. For example a candidate carrier may be produced by conventional peptide synthesis, conjugated with Taxol as described herein and tested in an in vivo model as described herein. A biologically active carrier may be identified, for example, based on its efficacy to increase survival of an animal which has been injected with tumor cells and treated with the conjugate compared to a control which has not been treated with a conjugate. Also a biologically active carrier may be identified based on its location in the parenchyma in an in situ cerebral perfusion assay.

It is to be understood herein, that if a "range" or "group of substances" is mentioned with respect to a particular characteristic (e.g., temperature, concentration, time and the like) of the present invention, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to a length of from 10 to 18 amino acid I, is to be understood as specifically incorporating herein each and every individual length, e.g., a length of 18, 17, 15, 10, and any number therebetween etc.; Therefore, unless specifically mentioned, every range mentioned herein is to be understood as being inclusive. For example, in the expression from 5 to 10 amino acids long is to be as including 5 and 10;

and similarly with respect to other parameters such as sequences, length, concentrations, elements, etc. . . .

It is in particular to be understood herein that the sequences, regions, portions defined herein each include each and every individual sequences, regions, portions described thereby as well as each and every possible sub-sequences, sub-regions, sub-portions whether such sub-sequences, sub-regions, sub-portions is defined as positively including particular possibilities, as excluding particular possibilities or a combination thereof; for example an exclusionary definition for a region may read as follows: "provided that said polypeptide is no shorter than 4, 5, 6, 7, 8 or 9 amino acids. Yet a further example of a negative limitation is the following; a sequence comprising SEQ ID NO.: X with the exclusion of a polypeptide of SEQ ID NO. Y; etc. An additional example of a negative limitation is the following; provided that said polypeptide is not (does not comprise or consist of) SEQ ID NO.:Z.

BRIEF DESCRIPTION OF THE DRAWINGS

In drawings which illustrates exemplary embodiments of the invention,

FIG. 9 illustrates the structure of exemplary polypeptides of the present invention.

DETAILED DESCRIPTION OF THE INVENTION

Figure 1:
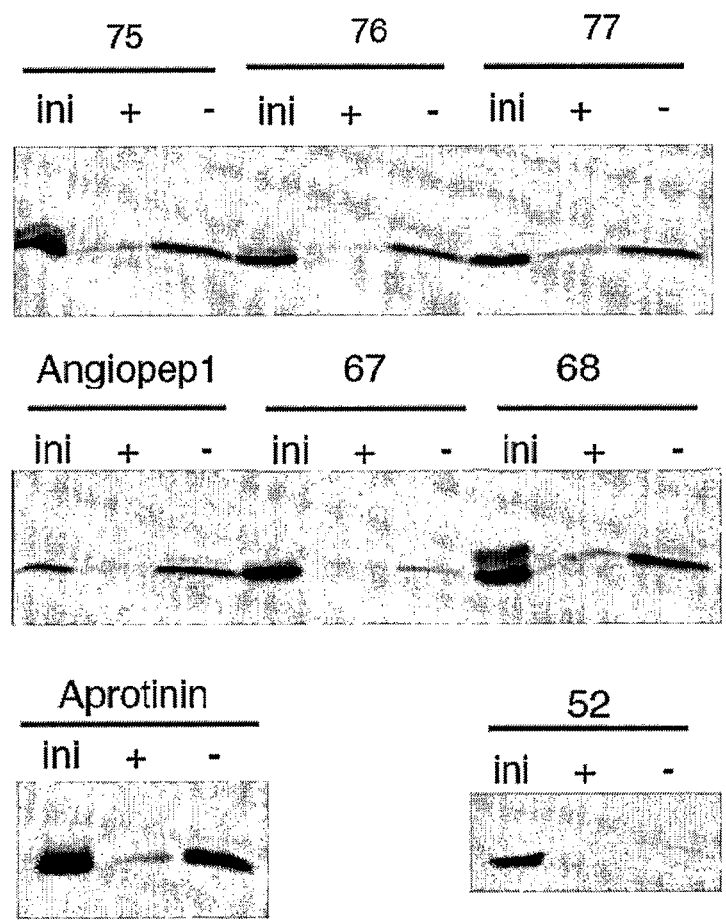
FIG. 1 illustrates an example of analysis using Tricine gels.

The present invention relates to new molecules that can act as vectors or carriers for transporting an agent, medicine or other molecule to the brain and/or central nervous system (CNS). Agents, medicines or other molecules that are unable or ineffective at crossing the blood-brain barrier by themselves will be transported across the blood-brain barrier when attached or coupled (conjugated) to the vector or carrier. Alternatively, an agent that is able to cross the blood-brain barrier by itself may also see its transport increase when conjugated to the carrier of the present invention. Such conjugates can be in the form of a composition, such as a pharmaceutical composition, for treatment of a condition or disease.

Design of Candidate Molecules as Carrier Vectors

In international publication no. WO2004/060403, the inventors have disclosed that AngioPep-1 (SEQ ID NO.:67) and aprotinin (SEQ ID NO.:98) are effective vectors for transporting desirable molecules across the blood brain barrier. The inventors herein demonstrate that other molecules could also be used as carriers for transporting an agent across the blood brain barrier. Accordingly, peptides having similar domains as aprotinine and Angiopep-1 and a modified form of Angiopep-1 (amidated, peptide no. 67) were therefore conceived as potential carrier vectors. These derived peptides resemble aprotinine and Angiopep-1 but comprise different amino acid insertions and bear different charges. Thus far, 96 peptides presented in Table 2 as well as additional peptides listed in the sequence listing were tested for their potential as carrier.

It is to be understood herein that in the following experiments, peptides have been selected based on their higher activity compared to others. Those which have not been selected for further experimentations are by no means being disclaimed and are not intended to be regarded as non-functional. These peptides show substantial activity and have utility has (biologically active) carriers and are also encompassed by the present invention.

TABLE 2

Design of 96 peptides from similar domain to aprotinine and Angiopep-1 with different charges and amino acid insertions

| Proteins | Characteristics | #Pep | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|---|
| Aprotk-synth | | 1 | T | F | V | Y | G | G | C | R | A | K | R | N | N | F | K | S | A | E | D | | | |
| Blkunin HI-30 | | 2 | T | F | Q | Y | G | G | C | M | G | N | G | N | N | F | V | T | E | K | E | | | |
| Amyloid | | 3 | P | F | F | Y | G | G | C | G | G | N | R | N | N | F | D | T | E | E | Y | | | |
| Kunitz-Inhib 1 | | 4 | S | F | Y | Y | G | G | C | G | G | N | R | N | N | F | D | T | E | E | Y | | | |
| Peptides | CHARGE (+6) | 5 | T | F | F | Y | G | G | C | R | A | K | R | N | N | F | K | R | A | K | Y | | | |
| | | 6 | T | F | F | Y | G | G | C | R | G | K | R | N | N | F | K | R | A | K | Y | | | |
| | | 7 | T | F | F | Y | G | G | C | R | A | K | K | N | N | Y | K | R | A | K | Y | | | |
| | | 8 | T | F | F | Y | G | G | C | R | G | K | K | N | N | F | K | R | A | K | Y | | | |
| | | 9 | T | F | Q | Y | G | G | C | R | A | K | R | N | N | F | K | R | A | K | Y | | | |
| | | 10 | T | F | Q | Y | G | G | C | R | G | K | K | N | N | F | K | R | A | K | Y | | | |
| | CHARGE (+5) | 11 | T | F | F | Y | G | G | C | L | G | K | R | N | N | F | K | R | A | K | Y | | | |
| | | 12 | T | F | F | Y | G | G | S | L | G | K | R | N | N | F | K | R | A | K | Y | | | |
| | | 13 | P | F | F | Y | G | G | C | G | G | K | K | N | N | F | K | R | A | K | Y | | | |
| | | 14 | T | F | F | Y | G | G | C | R | G | K | G | N | N | Y | K | R | A | K | Y | | | |
| | | 15 | P | F | F | Y | G | G | C | R | G | K | R | N | N | F | L | R | A | K | Y | | | |
| | | 16 | T | F | F | Y | G | G | C | R | G | K | R | N | N | F | K | R | E | K | Y | | | |
| | | 17 | P | F | F | Y | G | G | C | R | A | K | K | N | N | F | K | R | A | K | E | | | |
| | | 18 | T | F | F | Y | G | G | C | R | G | K | R | N | N | F | K | R | A | K | D | | | |
| | CHARGE (+4) | 19 | T | F | F | Y | G | G | C | R | A | K | R | N | N | F | D | R | A | K | Y | | | |
| | | 20 | T | F | F | Y | G | G | C | R | G | K | K | N | N | F | K | R | A | E | Y | | | |
| | | 21 | P | F | F | Y | G | G | C | G | A | N | R | N | N | F | K | R | A | K | Y | | | |
| | | 22 | T | F | F | Y | G | G | C | G | G | K | K | N | N | F | K | T | A | K | Y | | | |
| | | 23 | T | F | F | Y | G | G | C | R | G | N | R | N | N | F | L | R | A | K | Y | | | |
| | | 24 | T | F | F | Y | G | G | C | R | G | N | R | N | N | F | K | T | A | K | Y | | | |
| | | 25 | T | F | F | Y | G | G | S | R | G | N | R | N | N | F | K | T | A | K | Y | | | |
| | CHARGE (+3) | 26 | T | F | F | Y | G | G | C | L | G | N | G | N | N | F | K | R | A | K | Y | | | |
| | | 27 | T | F | F | Y | G | G | C | L | G | N | R | N | N | F | L | R | A | K | Y | | | |
| | | 28 | T | F | F | Y | G | G | C | L | G | N | R | N | N | F | K | T | A | K | Y | | | |
| | | 29 | T | F | F | Y | G | G | C | R | G | N | G | N | N | F | K | S | A | K | Y | | | |
| | | 30 | T | F | F | Y | G | E | C | R | G | K | K | N | N | F | D | R | E | K | Y | | | |

TABLE 2-continued

Design of 96 peptides from similar domain to aprotinine and
Angiopep-1 with different charges and amino acid insertions 96 PEPTIDES ORDERED AT SYNPEP (california, USA)

| Proteins | Characteristics | #Pep | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|---|
| | | 31 | T | F | F | Y | G | G | C | R | G | K | K | N | N | F | D | R | E | K | E | | | |
| | | 32 | T | F | F | Y | G | G | C | R | G | K | G | N | N | F | D | R | A | K | Y | | | |
| | | 33 | T | F | F | Y | G | G | S | R | G | K | G | N | N | F | D | R | A | K | Y | | | |
| | CHARGE (+2) | 34 | T | F | F | Y | G | G | C | R | G | N | G | N | N | F | V | T | A | K | Y | | | |
| | | 35 | P | F | F | Y | G | G | C | G | G | K | G | N | N | Y | V | T | A | K | Y | | | |
| | | 36 | T | F | F | Y | G | G | C | L | G | K | G | N | N | F | L | T | A | K | Y | | | |
| | | 37 | S | F | F | Y | G | G | C | L | G | N | K | N | N | F | L | T | A | K | Y | | | |
| | HUMAN | 38 | T | F | F | Y | G | G | C | G | G | N | K | N | N | F | V | R | E | K | Y | | | |
| | HUMAN | 39 | T | F | F | Y | G | G | C | M | G | N | K | N | N | F | V | R | E | K | Y | | | |
| | HUMAN | 40 | T | F | F | Y | G | G | S | M | G | K | N | N | F | V | R | E | K | Y | | | | |
| | HUMAN | 41 | P | F | F | Y | G | G | C | L | G | N | R | N | N | Y | V | R | E | K | Y | | | |
| | HUMAN | 42 | T | F | F | Y | G | G | C | L | G | N | R | N | N | F | V | R | E | K | Y | | | |
| | HUMAN | 43 | T | F | F | Y | G | G | C | L | G | N | K | N | N | Y | V | R | E | K | Y | | | |
| | CHARGE (+1) | 44 | T | F | F | Y | G | G | C | G | G | N | G | N | N | F | L | T | A | K | Y | | | |
| | | 45 | T | F | F | Y | G | G | C | R | G | N | R | N | N | F | L | T | A | E | Y | | | |
| | | 46 | T | F | F | Y | G | G | C | R | G | N | G | N | N | F | K | S | A | E | Y | | | |
| | | 47 | P | F | F | Y | G | G | C | L | G | N | K | N | N | F | K | T | A | E | Y | | | |
| | | 48 | T | F | F | Y | G | G | C | R | G | N | R | N | N | F | K | T | E | E | Y | | | |
| | | 49 | T | F | F | Y | G | G | C | R | G | K | N | N | N | F | K | T | E | E | D | | | |
| | HUMAN | 50 | P | F | F | Y | G | G | C | G | G | N | G | N | N | F | V | R | E | K | Y | | | |
| | HUMAN | 51 | S | F | F | Y | G | G | C | M | G | N | G | N | N | F | V | R | E | K | Y | | | |
| | HUMAN | 52 | P | F | F | Y | G | G | C | G | G | N | G | N | N | F | L | R | E | K | Y | | | |
| | HUMAN | 53 | T | F | F | Y | G | G | C | L | G | N | G | N | N | F | L | R | E | K | Y | | | |
| | HUMAN | 54 | S | F | F | Y | G | G | C | L | G | N | N | N | N | Y | L | R | E | K | Y | | | |
| | HUMAN | 55 | T | F | F | Y | G | G | S | L | G | N | G | N | N | F | V | R | E | K | Y | | | |
| | CHARGE (+0) | 56 | T | F | F | Y | G | G | C | R | G | N | G | N | N | F | V | T | A | E | Y | | | |
| | | 57 | T | F | F | Y | G | G | C | L | G | K | G | N | N | F | V | S | A | E | Y | | | |
| | | 58 | T | F | F | Y | G | G | C | L | G | N | R | N | N | F | D | R | A | E | Y | | | |
| | HUMAN | 59 | T | F | F | Y | G | G | C | L | G | N | R | N | N | P | L | R | E | E | Y | | | |
| | HUMAN | 60 | T | F | F | Y | G | G | C | L | G | N | K | N | N | Y | L | R | E | E | Y | | | |
| | HUMAN | 61 | P | F | F | Y | G | G | C | G | G | N | R | N | N | Y | L | R | E | E | Y | | | |
| | HUMAN | 62 | P | F | F | Y | G | G | S | G | G | N | R | N | N | Y | L | R | E | E | Y | | | |
| Aprotinin vs | APROTININ M-term | 63 | M | R | P | D | F | C | L | E | P | P | Y | T | G | P | C | V | A | R | I | | | |
| | (1 heilx α, A-term) | 64 | A | R | I | I | R | Y | F | Y | N | A | K | A | G | L | C | Q | T | F | V | Y | G | |
| | (2 βsheets, Y-term) | 65 | Y | G | G | C | R | A | K | R | N | N | Y | K | S | A | E | D | C | M | R | T | C | G |
| | (1 α, 1 β) | 66 | P | D | F | C | L | E | P | P | Y | T | G | P | C | V | A | R | I | I | R | Y | F | Y |
| AnglaFap | AngloPep-1 | 67 | T | F | F | Y | G | G | C | R | G | K | R | N | N | F | K | T | E | E | Y | | | |
| | AngloPEP1 (lyains) | 68 | K | F | F | Y | G | G | C | R | G | K | R | N | N | F | K | T | E | E | Y | | | |
| | AngloPEP1 (4Y) | 69 | T | F | Y | Y | G | G | C | R | G | K | R | N | N | Y | K | T | E | E | Y | | | |
| | cys bridge | 70 | T | F | F | Y | G | G | C | R | G | K | R | N | N | F | K | T | E | E | Y | | | |
| | cys-Nterminal | 71 | C | T | F | F | Y | G | C | C | R | G | K | R | N | N | F | K | T | E | E | Y | | |
| | cys-Cterminal | 72 | T | F | F | Y | G | G | C | R | G | K | R | N | N | F | K | T | E | E | Y | C | | |
| | cys-Nterminal | 73 | C | T | F | F | Y | G | S | C | R | G | K | R | N | N | F | K | T | E | E | Y | | |
| | cys-Cterminal | 74 | T | F | F | Y | G | G | S | R | G | K | R | N | N | F | K | T | E | E | Y | C | | |
| | pro | 75 | P | F | F | Y | G | G | C | R | G | K | R | N | N | F | K | T | E | E | Y | | | |
| | charge (+3) | 76 | T | F | F | Y | G | G | C | R | G | K | R | N | N | F | K | T | K | E | Y | | | |
| | charge (+3)-cys | 77 | T | F | F | Y | G | G | K | R | G | K | R | N | N | F | K | T | E | E | Y | | | |
| | charge (+4) | 78 | T | F | F | Y | G | G | C | R | G | K | R | N | N | F | K | T | K | R | Y | | | |
| | charge (+4)-cys | 79 | T | F | F | Y | G | G | K | R | G | K | R | N | N | F | K | T | A | E | Y | | | |
| | charge (+5) | 80 | T | F | F | Y | G | G | K | R | G | K | R | N | N | F | K | T | A | E | Y | | | |
| | charge (+6) | 81 | T | F | F | Y | G | G | K | R | G | K | R | N | N | F | K | R | E | K | Y | | | |
| | charge (+7) | 82 | T | F | F | Y | G | G | K | R | G | K | R | N | N | F | K | R | A | K | Y | | | |
| | charge (0) | 83 | T | F | F | Y | G | G | C | L | G | N | R | N | N | F | K | T | E | E | Y | | | |
| | permut cys(−) | 84 | T | F | F | Y | G | C | G | R | G | K | R | N | N | F | K | T | E | E | Y | | | |
| | permut cys(+) | 85 | T | F | F | Y | G | G | R | C | G | K | R | N | N | F | K | T | E | E | E | | | |
| | chargs(−4) | 86 | T | F | F | Y | G | G | C | L | G | N | G | N | N | F | D | T | E | E | E | | | |
| | Q Instead of F | 87 | T | F | Q | Y | G | G | C | R | G | K | R | N | N | F | K | T | E | E | Y | | | |
| | ANGIOPEP scramble | 88 | Y | N | K | E | F | G | T | F | N | T | K | G | C | E | R | G | Y | R | F | | | |
| TFPI | TFPI (similar domain) | 89 | R | F | K | Y | G | G | C | L | G | N | M | N | N | F | E | T | L | E | E | | | |
| | Chargs+5 (HUMAN) | 90 | R | F | K | Y | G | G | C | L | G | N | K | N | N | F | L | R | L | K | Y | | | |
| | Chargs+5 (HUMAN) | 91 | R | F | K | Y | G | G | C | L | G | N | K | N | N | Y | L | R | L | K | Y | | | |
| | TFPI (c-terminal) (2Y) | 92 | K | T | K | R | K | R | K | K | Q | R | V | K | I | A | Y | E | E | I | F | K | N | Y |
| | TFPI (c-terminal tronque) | 93 | K | T | K | R | K | R | K | K | Q | R | V | K | I | A | Y | | | | | | | |
| Basic = Peptides | SynB1 | 94 | R | G | G | R | L | S | Y | S | R | R | F | S | T | S | T | G | R | | | | | |
| | S7nB3 | 95 | R | R | L | S | Y | G | R | R | R | P | | | | | | | | | | | | |
| | Penetradin (pAntp43-68) | 96 | R | Q | I | K | I | W | F | Q | N | R | R | M | K | W | K | K | | | | | | |

Selection with In Vitro Model

An in vitro model was used as a screening assay and for mechanistic studies of drug transport to the brain. This efficient in vitro model of the blood-brain barrier was developed by the company CELLIAL™ Technologies. Yielding reproducible results, the in vitro model was used for evaluating the capacity of different carriers to reach the brain. The model consists of a co-culture of bovine brain capillary endothelial cells and rat glial cells. It presents ultrastructural features characteristic of brain endothelium including tight junctions, lack of fenestration, lack of transendothelial channels, low permeability for hydrophilic molecules and a high electrical resistance. Moreover, this model has shown a good correlation coefficient between in vitro and in vivo analyses of a wide range of molecules tested. To date, all the data obtained show that this BBB model closely mimics the in vivo situation by reproducing some of the complexities of the cellular environment that exist in vivo, while retaining the experimental advantages associated with tissue culture. Many studies have validated this cell co-culture as one of the most reproducible in vitro models of the BBB.

The in vitro model of BBB was established by using a co-culture of BBCECs and astrocytes. Prior to cell culture, plate inserts (Millicell-PC 3.0 µM; 30-mm diameter) were coated on the upper side with rat tail collagen. They were then set in six-well microplates containing the astrocytes and BBCECs were plated on the upper side of the filters in 2 mL of co-culture medium. This BBCEC medium was changed three times a week. Under these conditions, differentiated BBCECs formed a confluent monolayer 7 days later. Experiments were performed between 5 and 7 days after confluence was reached. The permeability coefficient for sucrose was measured to verify the endothelial permeability.

Primary cultures of mixed astrocytes were prepared from newborn rat cerebral cortex (Dehouck M. P., Meresse S., Delorme P., Fruchart J. C., Cecchelli, R. An Easier, Reproducible, and Mass-Production Method to Study the Blood-Brain Barrier In Vitro. *J. Neurochem*, 54, 1798-1801, 1990). Briefly, after removing the meninges, the brain tissue was forced gently through an 82 µm nylon sieve. Astrocytes were plated on six-well microplates at a concentration of $1.2 \times 10^5$ cells/mL in 2 mL of optimal culture medium (DMEM) supplemented with 10% heat inactivated fetal bovine serum. The medium was changed twice a week.

Bovine brain capillary endothelial cells (BBCECs) were obtained from Cellial Technologies. The cells were cultured in the presence of DMEM medium supplemented with 10% (v/v) horse serum and 10% heat-inactivated calf serum, 2 mM of glutamine, 50 µg/mL of gentamycin, and 1 ng/mL of basic fibroblast growth factor, added every other day.

Originally, at a first level of selection, 96 peptides as described in Table 2 were tested as carrier with the in vitro model of the BBB. Each peptide was added to the upper side of the inserts covered or non-covered with endothelial cells for 90 minutes at 37° C. After the incubation, the peptides in the lower side of the chambers were resolved by electrophoresis. Electrophoresis gels were stained with Coomassie blue to visualize the peptides as illustrated with some peptides (without limitation) in FIG. 1. AngioPep-1 (either SEQ ID NO.:67 or peptide no. 67 (amidated form)) is often used herein as a reference or for comparison purpose. In FIG. 1, each initial peptide applied to the upper side of the filters was loaded on electrophoresis gel (ini) as control. After 90 minutes of transcytosis, a volume of 50 µl from the basolateral side of the filters covered with endothelial cells (+) or non-covered (−) was also loaded on Tricine gels. To visualize the peptides gels were stained with Coomassie blue.

Following the first level of screening, peptides detected in the lower side of the chambers by Coomassie blue staining (5, 8, 45, 67, 70, 71, 72, 73, 74, 75, 76, 77, 78, 79, 81, 82, 90 and 91) were selected for further study with the iodinated peptides. Briefly, the selected peptides were iodinated with standard procedures using iodo-beads from Sigma. Two iodo-beads were used for each protein. These beads were washed twice with 3 ml of phosphate buffer (PB) on a Whatman™ filter and resuspended in 60 µl of PB. $^{125}$I (1 mCi) from Amersham-Pharmacia biotech was added to the bead suspension for 5 min at room temperature. The iodination for each peptide was initiated by adding 100 µg (80-100 µl) of the bead suspension. After an incubation of 10 min at room temperature, the supernatants were applied on a desalting column prepacked with 5 ml of cross-linked Dextran™ from Pierce and $^{125}$I-proteins were eluted with 10 ml of PBS. Fractions of 0.5 ml were collected and the radioactivity in 5 µl of each fraction was measured. Fractions corresponding to $^{125}$I-proteins were pooled and dialyzed against Ringer/Hepes buffer, pH 7.4. The efficiency of radiolabeling was between $0.6\text{-}1.0 \times 10^8$ cpm/100 µg of protein.

The iodinated peptides were also investigated with the in vitro model of the BBB. Each peptide was added to upper side of the inserts covered or non-covered with endothelial cells for 90 minutes at 37° C. After the incubation, peptides in the lower side of the chambers were TCA precipitated. Results were expressed as cpm ratios. For each [$^{125}$I]-peptide the number of cpm in the bottom chamber was divided by the total number of cpm added to filter covered with endothelial cells (+cells/initial) or uncovered (−cells/initial). The ratio between the number of [$^{125}$I]-peptide found in the bottom chamber of filters covered with or without endothelial cells was also calculated (+cells/−cells). A very low −cells/initial ratio indicates that filters may interfere with the peptides (peptides 5 and 8). A high +cells/initial and +cells/−cells ratio indicate a better passage of the peptides across the brain endothelial cells. The results for the previously selected 18 peptides are shown in Table 3.

TABLE 3

Results of the peptide screening following the second screening level

| | Ratios | | |
|---|---|---|---|
| #Peptides | −cells/initial | +cells/initial | +cells/−cells |
| 5 | 0.111 | 0.051 | 0.46 |
| 8 | 0.086 | 0.039 | 0.46 |
| 45 | 0.163 | 0.049 | 0.30 |
| 67 | 0.403 | 0.158 | 0.39 |
| 70 | 0.143 | 0.032 | 0.23 |
| 71 | 0.072 | 0.027 | 0.37 |
| 72 | 0.209 | 0.029 | 0.014 |
| 73 | 0.056 | 0.017 | 0.30 |
| 74 | 0.146 | 0.036 | 0.24 |
| 75 | 0.207 | 0.087 | 0.42 |
| 76 | 0.222 | 0.084 | 0.38 |
| 77 | 0.224 | 0.063 | 0.28 |
| 78 | 0.125 | 0.075 | 0.60 |
| 79 | 0.194 | 0.078 | 0.40 |
| 81 | 0.203 | 0.088 | 0.43 |
| 82 | 0.120 | 0.043 | 0.36 |
| 90 | 0.284 | 0.134 | 0.47 |
| 91 | 0.406 | 0.158 | 0.30 |
| Aprotinin | 0.260 | 0.022 | 0.08 |

From these results, 12 peptides with +cells/−cells ratios generally higher than 0.35 were selected namely; 5, 8, 67, 75, 76, 77, 78, 79, 81, 82, 90 and 91. Peptides #91 and #77 were also selected for further investigation because of their +cells/−cells ratios (>0.2).

The 12 selected peptides were then investigated by assessing their permeability coefficients using the in vitro BBB model. The effect of each selected peptide at 250 nM on the BBB integrity was determined by measuring [$^{14}$C] sucrose permeability in the BBB model on BBCEC monolayers grown on filters in the presence of astrocytes. To achieve this test, brain endothelial cell monolayers grown on inserts were transferred to 6-well plates containing 2 mL of Ringer-Hepes per well (basolateral compartment) for two hours at 37° C. Ringer-Hepes solution was composed of 150 mM NaCl, 5.2 mM KCl, 2.2 mM CaCl$_2$, 0.2 mM MgCl$_2$, 6 mM NaHCO$_3$, 5 mM Hepes, 2.8 mM Hepes, pH 7.4. In each apical chamber, the culture medium was replaced by 1 mL Ringer-Hepes containing the labeled [$^{14}$C]-sucrose. At different times, inserts were placed into another well. [$^{14}$C] sucrose passage was measured at 37° C., on filters without cells or with filters coated with BBCEC cells. The peptides are added at the start of the experiment at time zero. The results were plotted as the sucrose clearance (μl) as a function of time (min).

$$\text{Clearance } (\mu l) = \frac{[C]A \times VA}{[C]L}$$

[C]A = Abluminal tracer concentration

VA = Volume of abluminal chamber

[C]L = Luminal tracer concentration

The slope of the linear variation (μl/min) is the sucrose permeability coefficient for the filter without cells (Psf) and one with coated with BBCEC cells (PSt) in the presence of the peptide.

The permeability coefficient (Pe) was calculated as:

$$1/Pe = (1/PSt - 1/PSf)/\text{filter area } (4.2 \text{ cm}^2)$$

The peptides with highest Pe were selected: 67, 76, 90, 91, 5, 79, 8, and 78.

The in situ cerebral perfusion (in mice) was used as the fourth level of selection to select the best peptides. This procedure also distinguishes between compounds remaining in the brain vascular compartment from those having crossed the abluminal endothelial membrane to enter the brain parenchyma. Indeed, the technique of post-perfusion capillary depletion allows to measure whether the molecule really crosses the endothelium to enter the brain parenchyma. Using this technique it is demonstrated herein that specific peptides tend to accumulate in the brain parenchyma fraction (see Table 4).

TABLE 4

| | Volume of distribution (perfusion 5 min) | | | | |
|---|---|---|---|---|---|
| | Homogenate | Capillaries | | Parenchyma | |
| #Peptides | (ml/100 g) | (ml/100 g) | % | (ml/100 g) | % |
| 5 | 312 | 217 | 73 | 95 | 27 |
| 8 | 250 | 204 | 82 | 46 | 18 |
| 25 | 1141 | 1082 | 95 | 60 | 5 |
| 67 | 38 | 13 | 34 | 25 | 65 |
| 76 | 40 | 16 | 40 | 24 | 60 |
| 78 | 198 | 181 | 90 | 16 | 10 |
| 79 | 70 | 52 | 74 | 18 | 26 |
| 90 | 87 | 76 | 88 | 11 | 12 |
| 91 | 47 | 24 | 59 | 23 | 41 |

Four peptides, namely 5, 67, 76 and 91, showed the highest levels of distribution in the parenchyma with a volume higher than 20 ml/100 g and which represents at least 25% of the volume found for the total brain (homogenate), thus showing the highest potential as carrier for use as transport vectors. Peptide 79 was eliminated because of its lower volume of distribution in the brain parenchyma (18 ml/100 g). Peptide 67 represents the amidated form of AngioPep-1 described in the previous application that the inventors filed. Amidation of a peptide affect the overall charge of the peptide. As is apparent in Tables 2 and 3, two peptides having a different charge do not have necessary the same activity.

The vector or carrier of the present invention may thus be used in a method for transporting an agent across the blood-brain barrier comprises administering to an individual an agent that comprises an active ingredient or a pharmaceutical agent attached to a carrier, such as aprotinin or a functional derivative thereof (i.e., an aprotinin analog, an aprotinin fragment, an aprotin derivative, an analogue of an aprotinin fragment).

The carrier and conjugate may be administered intra-arterially, intra-nasally, intra-peritoneally, intravenously, intra-muscularly, sub-cutaneously, transdermally or per os to the patient. The agent may be, for example, an anti-angiogenic compound. The agent may have a maximum weight of 160, 000 Daltons. As discussed herein, the agent may be a marker or a drug such as a small molecule drug, a protein, a peptide or an enzyme. The drug may be adapted to treat, for example, a neurological disease or a central nervous system disorder of a patient. The drug may be a cytotoxic drug and the marker may be a detectable label such as a radioactive label, a green fluorescent protein, a histag protein or β-galactosidase. The agent may be delivered, for example, into the central nervous system of a patient.

According to another embodiment, the uses, methods, compounds, agents, drugs or medicaments therein mentioned may not alter the integrity of the blood-brain barrier of the patient.

According to a further embodiment of the present invention the peptide may be selected from the group consisting of aprotinin, an aprotinin fragment (SEQ ID NO.:1) and any one of the peptides defined in SEQ ID NO.:1 to 97, 99, 100 or 101.

For example, peptides 5, 76, 91, 97 and 97 as well as peptide 67 may be used in the present invention by linking them to an agent or a compound for transporting the agent or compound across the blood-brain barrier of a patient. The agent or compound may be adapted to treat a neurological disease or to treat a central nervous system disorder.

The carrier of the present invention, such as for example, peptides 5, 76, 91 and 97 as well as peptide 67 may be linked to or labelled with a detectable label such as a radioimaging agent, such as those emitting radiation, for detection of a disease or condition, for example by the use of a radioimaging agent-antibody-carrier conjugate, wherein the antibody binds to a disease or condition-specific antigen. Other binding molecules besides antibodies and which are known and used in the art are also contemplated by the present invention. Alternatively, the carrier or functional derivative thereof of the present invention or mixtures thereof may be linked to a therapeutic agent, to treat a disease or condition, or may be linked to or labelled with mixtures thereof. Treatment may be effected by administering a carrier-agent conjugate of the present invention to an individual under conditions which allow transport of the agent across the blood-brain barrier.

A therapeutic agent as used herein may be a drug, a medicine, an agent emitting radiation, a cellular toxin (for example, a chemotherapeutic agent) and/or biologically active fragment thereof, and/or mixtures thereof to allow cell killing or it may be an agent to treat, cure, alleviate, improve, diminish or inhibit a disease or condition in an individual treated. A therapeutic agent may be a synthetic product or a product of fungal, bacterial or other microorganism, such as mycoplasma, viral etc., animal, such as reptile, or plant origin. A therapeutic agent and/or biologically active fragment thereof may be an enzymatically active agent and/or fragment thereof, or may act by inhibiting or blocking an important and/or essential cellular pathway or by competing with an important and/or essential naturally occurring cellular component.

Examples of radioimaging agents emitting radiation (detectable radio-labels) that may be suitable are exemplified by indium-111, technitium-99, or low dose iodine-131.

Detectable labels, or markers, for use in the present invention may be a radiolabel, a fluorescent label, a nuclear magnetic resonance active label, a luminescent label, a chromophore label, a positron emitting isotope for PET scanner, chemiluminescence label, or an enzymatic label. Fluorescent labels include but are not limited to, green fluorescent protein (GFP), fluorescein, and rhodamine. Chemiluminescence labels include but are not limited to, luciferase and β-galactosidase. Enzymatic labels include but are not limited to peroxidase and phosphatase. A histag may also be a detectable label.

It is contemplated that an agent may be releasable from the carrier after transport across the blood-brain barrier, for example by enzymatic cleavage or breakage of a chemical bond between the carrier and the agent. The release agent may then function in its intended capacity in the absence of the carrier.

The present invention will be more readily understood by referring to the following examples which are given to illustrate the invention rather than to limit its scope. The following examples have been given with aprotinin. However, it has been demonstrated herein the molecules of the present invention share common properties with aprotinin with respect to their potential as carrier for transporting an agent across the blood brain barrier. These examples thus apply to the molecules of the present invention.

EXAMPLE I

Strategies for Drug Conjugation (Paclitaxel)

Figure 2:
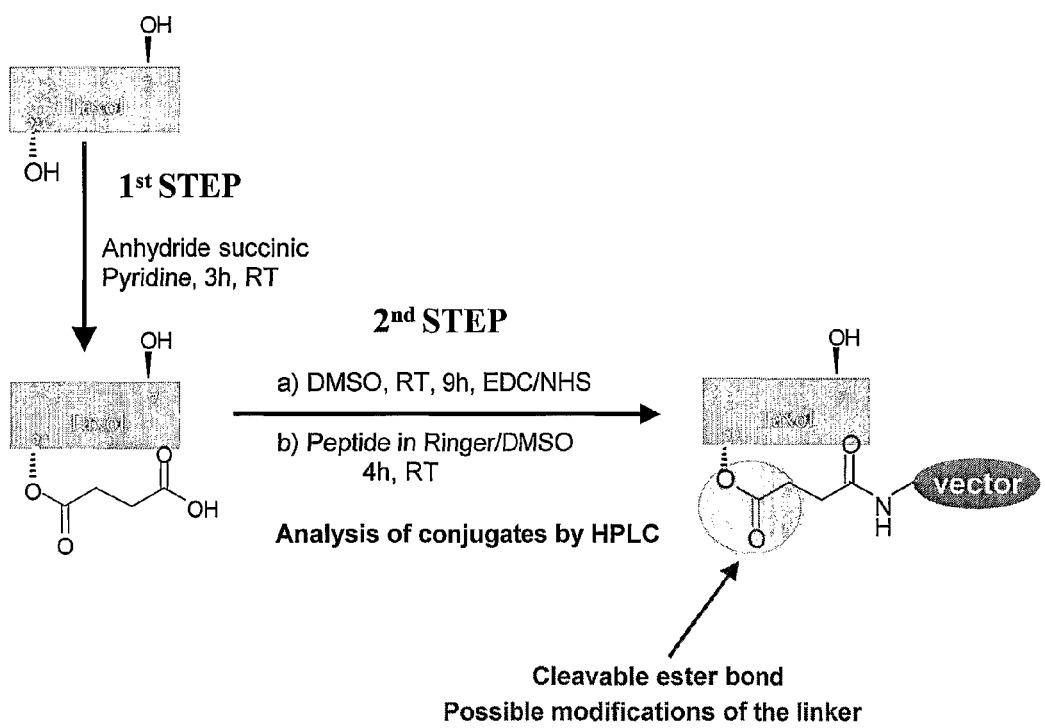
FIG. 2 illustrates the method of attachment of the vector or carrier of the present invention to paclitaxel.

For conjugation, paclitaxel (TAXOL™) has 2 strategic positions (position C2' and C7). FIG. 2 illustrates the method of attachment of the vector or carrier of the present invention to paclitaxel. Briefly, paclitaxel is reacted with anhydride succinic pyridine for 3 hours at room temperature to attach a succinyl group in position 2'. Such 2'-succinyl paclitaxel has a cleavable ester bond in position 2' which upon cleavage can simply release succinic acid. This cleavable ester bond can be further used for various modifications with linkers, if desired. The resulting 2'-O-succinyl-paclitaxel is then reacted with EDC/NHS in DMSO for 9 hours at room temperature, followed by the addition of the carrier or vector in Ringer/DMSO for an additional reaction time of 4 hours at room temperature. The reaction of conjugation depicted in FIG. 2 is monitored by HPLC. Each intermediate, such as paclitaxel, 2'-O-succinyl-paclitaxel and 2'-O—NHS-succinyl-paclitaxel, is purified and validated using different approaches such as HPLC, thin liquid chromatography, NMR ($^{13}$C or $^1$H exchange), melting point, mass spectrometry. The final conjugate is analyzed by mass spectrometry and SDS-polyacrylamide gel electrophoresis. This allows determining the number of paclitaxel molecules conjugated on each vector.

Transcytosis capacity of Aprotinin-Paclitaxel conjugate was determined and is reported below in Table 5.

TABLE 5

Determination of aprotinin-Taxol conjugate transcytosis capacity across the BBB

|  | Transcytosis (Pe $10^{-3}$ cm/min) | Sucrose Integrity (Pe $10^{-3}$ cm/min) |
| --- | --- | --- |
| Control |  |  |
| Aprotinin | 0.2 | 0.28 |
| Aprotinin-Taxol | 0.21 | 0.24 |
|  |  | 0.22 |

Conjugation does not affect the aprotinin capacity to cross the barrier
The integrity of the barrier is also maintained As seen in Table 5, conjugation of paclitaxel to aprotinin still was able to cross the in vitro model of the blood brain barrier without affecting the sucrose integrity, thus proving that the molecules (also referred herein as vectors or carriers) of the present invention still retain their activity when conjugated to a large chemical entity such as paclitaxel.

Figure 3:
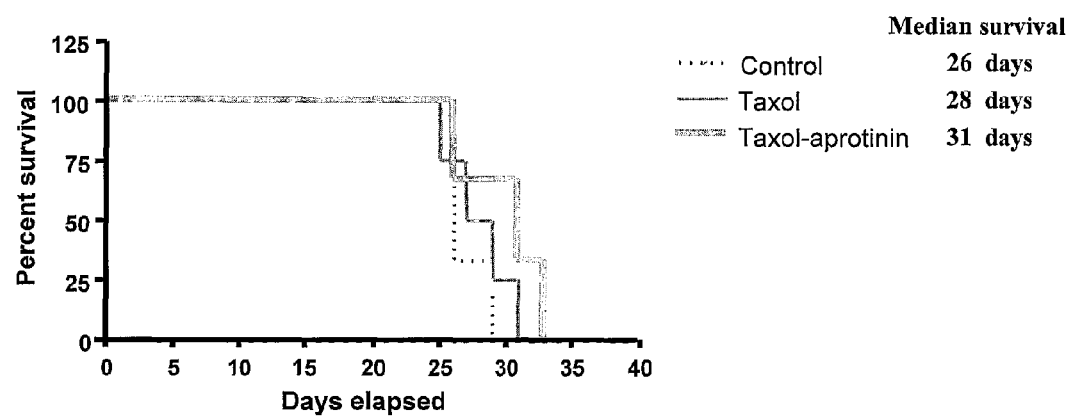
FIG. 3 illustrates the effect of treatment of glioblastoma model in Lewis rats with paclitaxel conjugated to aprotinin.

Survival study in the rat brain tumor model was then conducted to verify whether the paclitaxel that was conjugated is still active in vivo. For the rat brain tumor model, rats received an intra-cerebral implantation of 50 000 CNS-1 glioma cells. Three (3) days after, animals received treatment with vehicle (aprotinin), Paclitaxel (5 mg/kg) or Paclitaxel-Aprotinin (5 mg/kg) by intravenous injection. Treatment was then administered every week until animal was sacrificed (see FIG. 3). Rats were monitored every day for clinical symptoms and weight loss. According to the protocol of good animal practice, animals were sacrificed when a weight loss was observed for 3 consecutive days or before if the weight loss was more than 20% of the animal initial weight.

Using the same experimental protocol, paclitaxel when injected alone at the maximal tolerated dose (54 mg/kg) was unable to increase mouse survival (Laccabue et al., 2001 Cancer, 92 (12): 3085-92).

Figure 4:
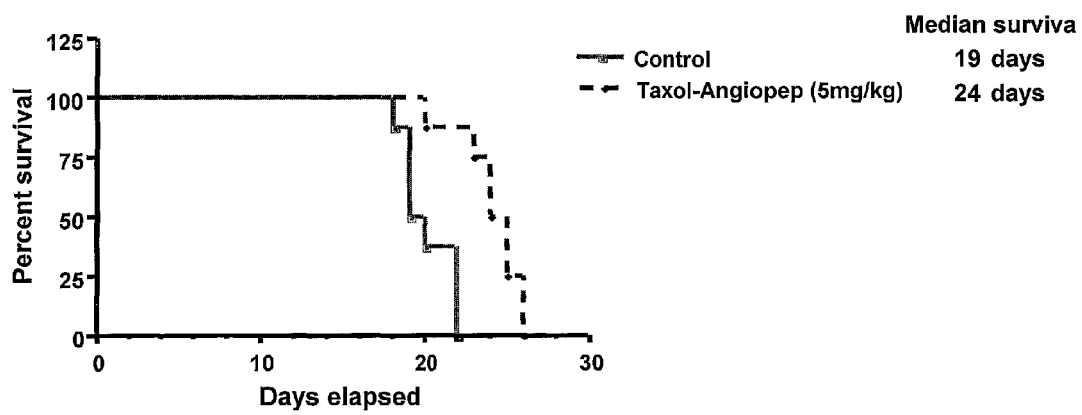
FIG. 4 illustrates the effect of treatment of glioblastoma model in nude mice with paclitaxel conjugated to AngioPep-1.

Survival study was also conducted in mice implanted with a human brain tumor xenograft. For the mice brain tumor model, mice received an intra-cerebral implantation of 500 000 human U87 glioma cells. 3 days after implantation animals received treatment with Paclitaxel-Angiopep1 (5 mg/kg) or vehicle by intravenous injection. Treatment was then administered every week until animal was sacrificed. Mice were monitored every day for clinical symptoms and weight loss. According to the protocol of good animal practice, animals were sacrificed when a weight loss was observed for 3 consecutive days or before if the weight loss was more than 20% of the animal initial weight. It was now observed that the medium survival for the control group was 19±2 days. For the statistical analysis a 20% increase in survival was considered significant. As can be seen in FIG. 4, the conjugate Paclitaxel-AngioPep-1 retained its activity, having a statistically significant effect. The survival time of the paclitaxel-angioPep1 treated animals is significantly extended when compared to control group ($p<0.05$, n=8).

Results obtained in the two survival studies indicate that the conjugation of paclitaxel with the vector of the present invention increases the animal survival.

EXAMPLE II

Strategies for Antibodies Conjugation

Since proteins generally have several amino groups available for conjugation, amine coupling using sulfo-NHS/EDC activation can be used to cross-link therapeutic antibodies with the vectors (carriers) of the present invention. This approach was chosen because it is a fast, simple and reproducible coupling technique, and because the resulting conjugate is stable while still retaining the biological activity of the antibody. It also has a high conjugation capacity that can be reliably controlled and a low non-specific interaction during the coupling procedures.

Antibodies or antibody fragments (Fab and F(ab')$_2$) have been conjugated with the vector of the present invention to increase their delivery to the brain. Various conjugation approaches have been used to first conjugate IgGs with aprotinin, having proven that the carriers of the present invention behave exactly as aprotinin.

Different cross-linkers, such as BS$^3$ [Bis(sulfosuccinimidyl)suberate], NHS/EDC (N-hydroxysuccinimide and N-ethyl-N'(dimethylaminopropyl)carbodimide or Sulfo-EMCS ([N-e-Maleimidocaproic acid]hydrazide) have been tested for the conjugation of IgG. BS$^3$ is a Homobifunctional N-hydroxysuccinimide ester that targets accessible primary amines. NHS/EDC creates a conjugation of primary amine groups with carboxyl groups. Sulfo-EMCS are heterobifunctional reactive groups (maleimide and NHS-ester) that are reactive toward: sulfhydryl and amino groups.

Figure 5:
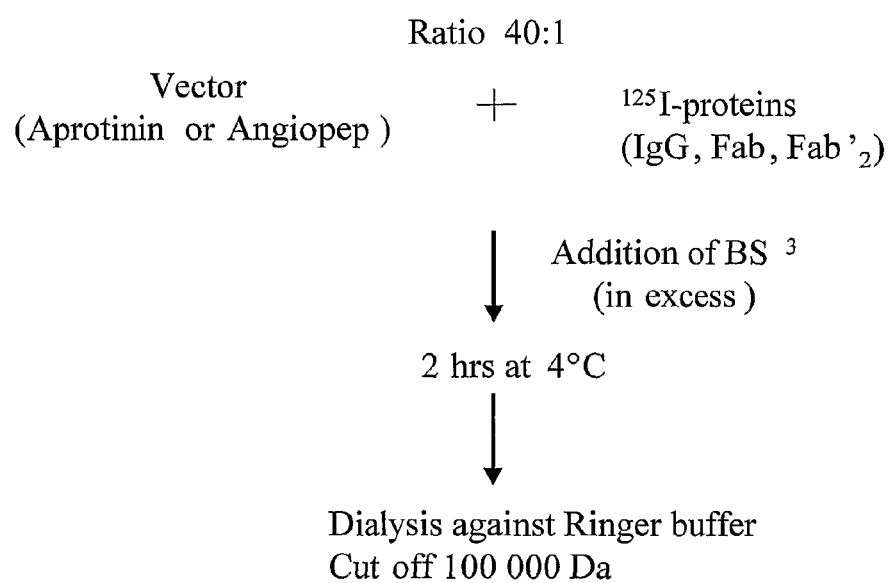
FIG. 5 illustrates the protocol used to conjugate aprotinin with IgG using cross-linker BS$^3$.
Figure 6:
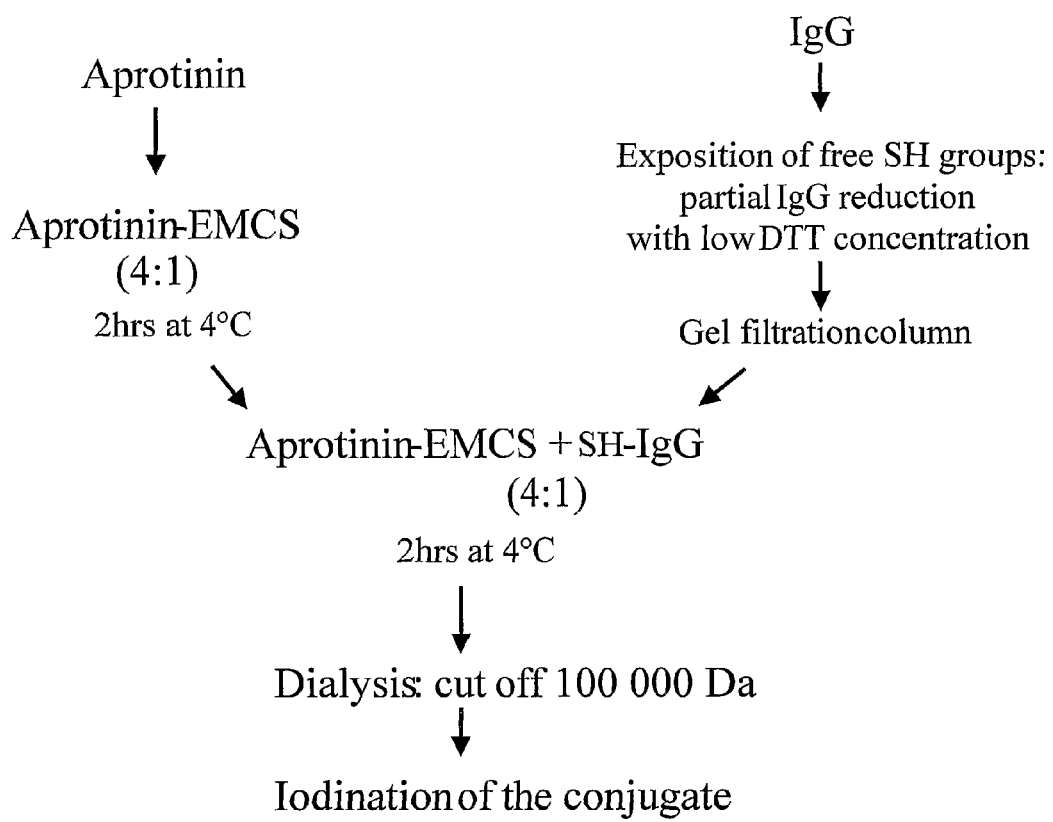
FIG. 6 illustrates the protocol used to conjugate aprotinin with IgG using cross-linker sulfo-EMCS.

Conjugation of IgG with aprotinin using the cross-linker BS$^3$ (FIG. 5) or sulfo-EMCS (FIG. 6) was first assessed.

Transport of IgG or IgG-conjugates across the BBB was then tested. The uptake of [$^{125}$I]-IgG to the luminal side of mouse brain capillaries was measured using the in situ brain perfusion method adapted in the inventor's laboratory for the study of drug uptake in the mouse brain (Dagenais et al., 2000, J. Cereb. Blood Flow Metab. 20(2):381-386). The BBB transport constants were determined as previously described by Smith (1996, Pharm. Biotechnol. 8:285-307). IgG uptake was expressed as the volume of distribution (Vd) from the following equation:

$$Vd = Q^*br/C^*pf$$

where $Q^*br$ is the calculated quantity of [$^{125}$I]-IgG or [$^{125}$I]-IgG-aprotinin conjugate per gram of right brain hemisphere and $C^*pf$ is the labelled tracer concentration measured in the perfusate.

Figure 7:
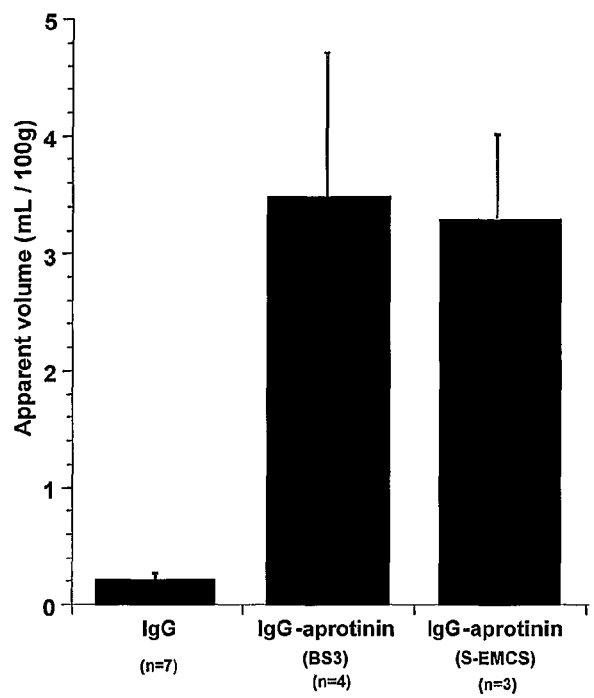
FIG. 7 illustrates the brain penetration for IgG-aprotinin conjugates.

The results of this experiment indicate that there is higher brain uptake for [$^{125}$I]-IgG-aprotinin conjugate than that of unconjugated [$^{125}$I]-IgG (see FIG. 7).

The conjugation of IgGs with aprotinin increases their accumulation in the brain parenchyma in vivo.

EXAMPLE III

Effect of Taxol-Angiopep-2 Conjugate on Mice Survival

Figure 8:
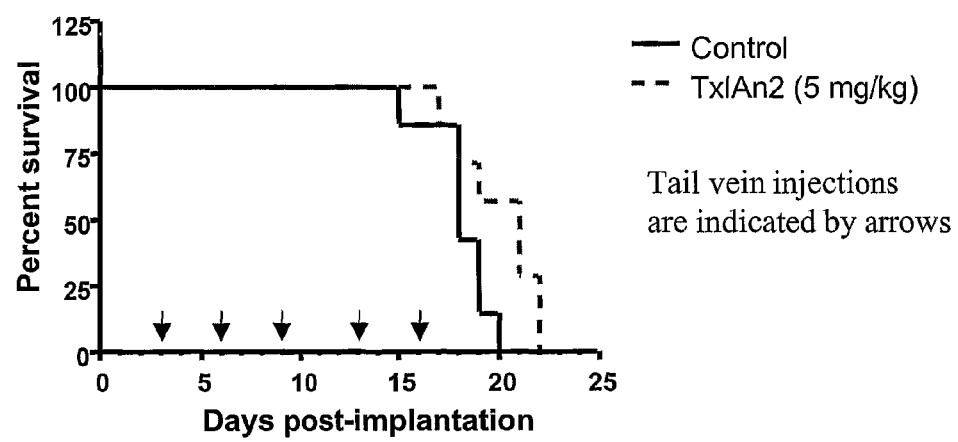
FIG. 8 illustrates the effect of treatment of Taxol-Angiopep-2 conjugate on the survival of glioblastoma-implanted mice (athymic, nude mice)

This study with Taxol-Angiopep-2 (herein referred to peptide no. 97 (angiopep2 is not amidated) was conducted to determine whether conjugation of Taxol to Angiopep-2 could increase mice survival. The structure of Angiopep-2 is illustrated in SEQ ID NO.:97. For this experiment, mice received an intra-cerebral implantation of 500 000 human U87 glioma cells. After 3 days following implantation, animals were treated with the vehicle (DMSO/Ringer-Hepes 80:20 v/v (i.e., control)) or Taxol-Angiopep-2 conjugate (3:1, i.e., ratio of 3 Taxol molecules for each peptide; TxlAn2 (5 mg/kg)) by tail vein injections (FIG. 8). Mice were monitored every day for clinical symptoms and weight loss. Treatments were administered until animals were sacrificed. As shown in Table 6, we observed that the median survival was 18 days for the control group whereas the median survival for mice receiving the Taxol-Angiopep-2 conjugate was 21 days (FIG. 8). Survival curve obtained for mice treated with Taxol-Angiopep-2 conjugate (in red) indicates that the median survival was significantly increased by 17% (FIG. 8). The statistical analysis presented also in Table 6 indicates that administration of Taxol-Angiopep-2 conjugate significantly increased survival by 17% (p values=0.048).

TABLE 6

Results summary of the survival study

| a. Median survival | Days | Increased (%) | Mice (n) |
|---|---|---|---|
| Control | 18.0 | — | 7 |
| TxlAn2 conjugate | 21.0 | +17 | 7 |

| b. Statistical analysis | (p values) | Stat. differences |
|---|---|---|
| Control vs Txlan2 conjugate | p = 0.048 | Yes |

The content of each publication, patent and patent application mentioned in the present application is incorporated herein by reference.

Although the present invention has been described in detail herein and illustrated in the accompanying drawings, it is to be understood that the invention is not limited to the embodiments described herein and that various changes and modifications may be effected without departing from the scope or spirit of the present invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

SEQUENCES

SEQ ID NO. :

1  T F V Y G G C R A K R N N F K S A E D

2  T F Q Y G G C M G N G N N F V T E K E

3  P F F Y G G C G G N R N N F D T E E Y

4  S F Y Y G G C L G N K N N Y L R E E E

5  T F F Y G G C R A K R N N F K R A K Y
Peptide no. 5 comprises the amino acid
sequence defined in SEQ ID NO.: 5 and
is amidated at its N-terminus
(see for example FIG. 9)

6  T F F Y G G C R G K R N N F K R A K Y

7  T F F Y G G C R A K K N N Y K R A K Y

8  T F F Y G G C R G K K N N F K R A K Y

9  T F Q Y G G C R A K R N N F K R A K Y

10 T F Q Y G G C R G K K N N F K R A K Y

11 T F F Y G G C L G K R N N F K R A K Y

| SEQ ID NO. : | Sequence |
|---|---|
| 12 | T F F Y G G S L G K R N N F K R A K Y |
| 13 | P F F Y G G C G G K K N N F K R A K Y |
| 14 | T F F Y G G C R G K G N N Y K R A K Y |
| 15 | P F F Y G G C R G K R N N F L R A K Y |
| 16 | T F F Y G G C R G K R N N F K R E K Y |
| 17 | P F F Y G G C R A K K N N F K R A K E |
| 18 | T F F Y G G C R G K R N N F K R A K D |
| 19 | T F F Y G G C R A K R N N F D R A K Y |
| 20 | T F F Y G G C R G K K N N F K R A E Y |
| 21 | P F F Y G G C G A N R N N F K R A K Y |
| 22 | T F F Y G G C G G K K N N F K T A K Y |
| 23 | T F F Y G G C R G N R N N F L R A K Y |
| 24 | T F F Y G G C R G N R N N F K T A K Y |
| 25 | T F F Y G G S R G N R N N F K T A K Y |
| 26 | T F F Y G G C L G N G N N F K R A K Y |
| 27 | T F F Y G G C L G N R N N F L R A K Y |
| 28 | T F F Y G G C L G N R N N F K T A K Y |
| 29 | T F F Y G G C R G N G N N F K S A K Y |
| 30 | T F F Y G G C R G K K N N F D R E K Y |
| 31 | T F F Y G G C R G K R N N F L R E K E |
| 32 | T F F Y G G C R G K G N N F D R A K Y |
| 33 | T F F Y G G S R G K G N N F D R A K Y |
| 34 | T F F Y G G C R G N G N N F V T A K Y |
| 35 | P F F Y G G C G G K G N N Y V T A K Y |
| 36 | T F F Y G G C L G K G N N F L T A K Y |
| 37 | S F F Y G G C L G N K N N F L T A K Y |
| 38 | T F F Y G G C G G N K N N F V R E K Y |
| 39 | T F F Y G G C M G N K N N F V R E K Y |
| 40 | T F F Y G G S M G N K N N F V R E K Y |
| 41 | P F F Y G G C L G N R N N Y V R E K Y |
| 42 | T F F Y G G C L G N R N N F V R E K Y |
| 43 | T F F Y G G C L G N K N N Y V R E K Y |
| 44 | T F F Y G G C G G N G N N F L T A K Y |
| 45 | T F F Y G G C R G N R N N F L T A E Y |
| 46 | T F F Y G G C R G N G N N F K S A E Y |
| 47 | P F F Y G G C L G N K N N F K T A E Y |
| 48 | T F F Y G G C R G N R N N F K T E E Y |
| 49 | T F F Y G G C R G K R N N F K T E E D |
| 50 | P F F Y G G C G G N G N N F V R E K Y |
| 51 | S F F I G G C M G N N N F V R E K Y |
| 52 | P F F Y G G C G G N G N N F L R E K Y |
| 53 | T F F Y G G C L G N G N N F V R E K Y |
| 54 | S F F Y G G C L G N G N N Y L R E K Y |
| 55 | T F F Y G G S L G N G N N F V R E K Y |
| 56 | T F F Y G G C R G N G N N F V T A E Y |
| 57 | T F F Y G G C L G K G N N F V S A E Y |
| 58 | T F F Y G G C L G N R N N F D R A E Y |
| 59 | T F F Y G G C L G N R N N F L R E E Y |
| 60 | T F F Y G G C L G N K N N Y L R E E Y |
| 61 | P F F Y G G C G G N R N N Y L R E E Y |
| 62 | P F F Y G G S G G N R N N Y L R E E Y |
| 63 | M R P D F C L E P P Y T G P C V A R I |
| 64 | A R I I R Y F Y N A K A G L C Q T F V Y G |
| 65 | Y G G C R A K R N N Y K S A E D C M R T C G |
| 66 | P D F C L E P P Y T G P C V A R I I R Y F Y |
| 67 | T F F Y G G C R G K R N N F K T E E Y |

The peptide no. 67 comprises the amino acid sequence defined in SEQ ID NO.: 67 and is amidated at its N-terminus (see for example FIG. 9)

| 68 | K F F Y G G C R G K R N N F K T E E Y |
|---|---|
| 69 | T F Y Y G G C R G K R N N Y K T E E Y |
| 70 | T F F Y G G S R G K R N N F K T E E Y |
| 71 | C T F F Y G C C R G K R N N F K T E E Y |
| 72 | T F F Y G G C R G K R N N F K T E E Y C |
| 73 | C T F F Y G S C R G K R N N F K T E E Y |
| 74 | T F F Y G G S R G K R N N F K T E E Y C |
| 75 | P F F Y G G C R G K R N N F K T E E Y |
| 76 | T F F Y G G C R G K R N N F K T K E Y |

The peptide no. 76 comprises the amino acid sequence defined in SEQ ID NO.: 76 and is amidated at its N-terminus (see for example FIG. 9).

| 77 | T F F Y G G K R G K R N N F K T E E Y |
|---|---|
| 78 | T F F Y G G C R G K R N N F K T K R Y |
| 79 | T F F Y G G K R G K R N N F K T A E Y |
| 80 | T F F Y G G K R G K R N N F K T A G Y |
| 81 | T F F Y G G K R G K R N N F K R E K Y |

| SEQ ID NO.: | |
|---|---|
| 81 | T F F Y G G C G G N G N N F L T A K Y |
| 82 | T F F Y G G C R G N R N N F L T A E Y |
| 83 | T F F Y G G C R G N G N N F K S A E Y |
| 84 | P F F Y G G C L G N K N N F K T A E Y |
| 85 | T F F Y G G C R G N R N N F K T E E Y |
| 86 | T F F Y G G C R G K R N N F K T E E D |
| 87 | P F F Y G G C G G N G N N F V R E K Y |
| 88 | R F K Y G G C L G N M N N F E T L E E |
| 89 | R F K Y G G C L G N K N N F L R L K Y |
| 91 | R F K Y G G C L G N K N N Y L R L K Y |

Peptide no. 91 comprises the amino acid sequence defined in SEQ ID NO.: 91 and is amidated at its N-terminus (see for example FIG. 9).

| | |
|---|---|
| 92 | K T K R K R K K Q R V K I A Y E E I F K N Y |
| 93 | K T K R K R K K Q R V K I A Y |
| 94 | R G G R L S Y S R R F S T S T G R |
| 95 | R R L S Y S R R R F |

| SEQ ID NO.: | |
|---|---|
| 96 | R Q I K I W F Q N R R M K W K K |
| 97 | T F F Y G G S R G K R N N F K T E E Y |
| 98 | M R P D F C L E P P Y T G P C V A R I I R Y F Y N A K A G L C Q T F V Y G G C R A K R N N F K S A E D C M R T C G G A |
| 99 | T F F Y G G C R G K R N N F K T K E Y |
| 100 | R F K Y G G C L G N K N N Y L R L K Y |
| 101 | T F F Y G G C R A K R N N F K R A K Y |
| 102 | N A K A G L C Q T F V Y G G C L A K R N N F E S A E D C M R T C G G A |
| 103 | Y G G C R A K R N N F K S A E D C M R T C G G A |
| 104 | G L C Q T F V Y G G C R A K R N N F K S A E |
| 105 | L C Q T F V Y G G C E A K R N N F K S A |

SEQ ID NO.: 106
atgagaccag atttctgcct cgagccgccg
tacactgggc cctgcaaagc tcgtatcatc
cgttacttct acaatgcaaa ggcaggcctg
tgtcagacct tcgtatacgg cggctgcaga
gctaagcgta acaacttcaa atccgcggaa
gactgcatgc gtacttgcgg tggtgcttag

---

The invention claimed is:

1. A method for treating a mammal having a neurological disease,
the method comprising administering to the mammal a conjugate comprising:
(a) a polypeptide comprising an amino acid sequence having at least 80% identity to the sequence of Angiopep-1 (SEQ ID NO:67), wherein the polypeptide has a substitution at the position corresponding to the cysteine at position 7 of the Angiopep-1 sequence; and
(b) an antibody or a biologically active fragment thereof for treating the neurological disease, wherein the antibody or the biologically active fragment thereof is conjugated to the polypeptide, and the conjugate is capable of crossing the blood-brain barrier or an in vitro model thereof.

2. The method of claim 1, wherein the neurological disease is a brain cancer, a brain metastasis, schizophrenia, epilepsy, Alzheimer's disease, Parkinson's disease, Huntington's disease, stroke, or obesity.

3. The method of claim 2, wherein the brain cancer is a glioma.

4. The method of claim 3, wherein the glioma is a glioblastoma.

5. The method of claim 1, wherein the polypeptide comprises an amino acid sequence having at least 85% identity to the sequence of Angiopep-1 (SEQ ID NO:67).

6. The method of claim 5, wherein the polypeptide comprises an amino acid sequence having at least 90% identity to the sequence of Angiopep-1 (SEQ ID NO:67).

7. The method of claim 1, wherein the substitution is the substitutition of a serine at the position corresponding to the cysteine at position 7.

8. The method of claim 7, wherein the polypeptide comprises the amino acid sequence of Angiopep-2 (SEQ ID NO:97).

9. The method of claim 7, wherein the polypeptide consists of the amino acid sequence of Angiopep-2 (SEQ ID NO:97).

10. The method of claim 1, wherein the antibody or the biologically active fragment thereof is a chemotherapeutic agent.

11. The method of claim 1, wherein the administration is intra-arterial, intra-nasal, intra-peritoneal, intravenous, intramuscular, subcutaneous, transdermal, or per os.

12. The method of claim 1, wherein the biologically active fragment of the antibody comprises an Fv fragment, an F(ab')2 fragment, or an Fab fragment.

13. The method of claim 1, wherein the conjugate further comprises a detectable label.

14. The method of claim 13, wherein the detectable label comprises a radioimaging agent, an isotope, a fluorescent label, a nuclear magnetic resonance label, a luminescent label, a chromophore, a chemiluminescent label, or an enzymatic label.

15. The method of claim 14, wherein the detectable label comprises a green fluoresence protein, a histag, β-galactosidase, indium-11, technitium-99, iodine-131, a peroxidase, or a phosphatase.

16. The method of claim 1, wherein the conjugate further comprises a linker.

17. The method of claim 16, wherein the linker is chemical in nature.

18. The method of claim 1, wherein the polypeptide and the antibody or the biologically active fragment thereof are joined in a fusion protein.

19. A method for transporting an antibody or a biologically active fragment thereof across the blood-brain barrier of a mammal, the method comprising administering to the mammal a conjugate comprising:
(a) a polypeptide comprising an amino acid sequence having at least 80% identity to the sequence of Angiopep-1 (SEQ ID NO:67), wherein the polypeptide has a substitution at the position corresponding to the cysteine at position 7 of the Angiopep-1 sequence; and
(b) the antibody or the biologically active fragment thereof, wherein the antibody or the biologically active fragment thereof is conjugated to the polypeptide, and the conjugate is capable of crossing the blood-brain barrier or an in vitro model thereof.

20. The method of claim 19, wherein the polypeptide comprises an amino acid sequence having at least 85% identity to the sequence of Angiopep-1 (SEQ ID NO:67).

21. The method of claim 19, wherein the polypeptide comprises an amino acid sequence having at least 90% identity to the sequence of Angiopep-1 (SEQ ID NO:67).

22. The method of claim 19, wherein the substitution is the substitution of a serine at the position corresponding to the cysteine at position 7.

23. The method of claim 22, wherein the polypeptide comprises the amino acid sequence of Angiopep-2 (SEQ ID NO:97).

24. The method of claim 23, wherein the polypeptide consists of the amino acid sequence of Angiopep-2 (SEQ ID NO:97).

25. The method of claim 19, wherein the conjugate further comprises a detectable label.

26. The method of claim 25, wherein the detectable label comprises a radioimaging agent, an isotope, a fluorescent label, a nuclear magnetic resonance label, a luminescent label, a chromophore, a chemiluminescent label, or an enzymatic label.

27. The method of claim 26, wherein the detectable label comprises a green fluoresence protein, a histag, β-galactosidase, indium-11, technitium-99, iodine-131, a peroxidase, or a phosphatase.

28. The method of claim 19, wherein the administration is intra-arterial, intra-nasal, intra-peritoneal, intravenous, intramuscular, subcutaneous, transdermal, or per os.

29. The method of claim 19, wherein the biologically active fragment of the antibody comprises an Fv fragment, an F(ab')2 fragment, or an Fab fragment.

30. The method of claim 19, wherein the conjugate further comprises a linker.

31. The method of claim 30, wherein the linker is chemical in nature.

32. The method of claim 19, wherein the polypeptide and the antibody or the biologically active fragment thereof are joined in a fusion protein.

33. A method of treating a patient having brain cancer, the method comprising administering to the patient a conjugate comprising:
(a) a polypeptide comprising Angiopep-2 (SEQ ID NO:97); and
(b) an antibody or a biologically active fragment thereof, wherein the antibody or the biologically active fragment thereof is conjugated to the Angiopep-2.

34. The method of claim 33, wherein administering the conjugate comprises intravenous administration.

35. The method of claim 33, wherein the conjugate further comprises a linker.

36. The method of claim 35, wherein the linker is chemical in nature.

37. The method of claim 33, wherein the polypeptide and the antibody or the biologically active fragment thereof are joined in a fusion protein.

* * * * *

SEQUENCE LISTING

<160> NUMBER OF SEQ ID NOS: 106

<210> SEQ ID NO 1
<211> LENGTH: 19
<212> TYPE: PRT
<213> ORGANISM: Artificial Sequence
<220> FEATURE:
<223> OTHER INFORMATION: An aprotinin fragment: Aprot-synth

<400> SEQUENCE: 1

Thr Phe Val Tyr Gly Gly Cys Arg Ala Lys Arg Asn Asn Phe Lys Ser
1               5                   10                  15

Ala Glu Asp

<210> SEQ ID NO 2
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Bikunin HI-30

<400> SEQUENCE: 2

Thr Phe Gln Tyr Gly Gly Cys Met Gly Asn Gly Asn Asn Phe Val Thr
1               5                   10                  15

Glu Lys Glu

<210> SEQ ID NO 3
<211> LENGTH: 19
<212> TYPE: PRT

```
<213> ORGANISM: Artificial Sequence
<220> FEATURE:
<223> OTHER INFORMATION: A peptide similar to aprotinine and Angiopep-1:
      Amyloid

<400> SEQUENCE: 3

Pro Phe Phe Tyr Gly Gly Cys Gly Gly Asn Arg Asn Asn Phe Asp Thr
1               5                   10                  15

Glu Glu Tyr

<210> SEQ ID NO 4
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Kunitz-Inhib 1

<400> SEQUENCE: 4

Ser Phe Tyr Tyr Gly Gly Cys Leu Gly Asn Lys Asn Asn Tyr Leu Arg
1               5                   10                  15

Glu Glu Glu

<210> SEQ ID NO 5
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+6)
<220> FEATURE:
<221> NAME/KEY: MISC_FEATURE
<223> OTHER INFORMATION: may be amidated

<400> SEQUENCE: 5

Thr Phe Phe Tyr Gly Gly Cys Arg Ala Lys Arg Asn Asn Phe Lys Arg
1               5                   10                  15

Ala Lys Tyr

<210> SEQ ID NO 6
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+6)

<400> SEQUENCE: 6

Thr Phe Phe Tyr Gly Gly Cys Arg Gly Lys Arg Asn Asn Phe Lys Arg
1               5                   10                  15

Ala Lys Tyr

<210> SEQ ID NO 7
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+6)

<400> SEQUENCE: 7

Thr Phe Phe Tyr Gly Gly Cys Arg Ala Lys Lys Asn Asn Tyr Lys Arg
1               5                   10                  15

Ala Lys Tyr
```

-continued

```
<210> SEQ ID NO 8
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+6)

<400> SEQUENCE: 8

Thr Phe Phe Tyr Gly Gly Cys Arg Gly Lys Lys Asn Asn Phe Lys Arg
1               5                   10                  15

Ala Lys Tyr

<210> SEQ ID NO 9
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+6)

<400> SEQUENCE: 9

Thr Phe Gln Tyr Gly Gly Cys Arg Ala Lys Arg Asn Asn Phe Lys Arg
1               5                   10                  15

Ala Lys Tyr

<210> SEQ ID NO 10
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+6)

<400> SEQUENCE: 10

Thr Phe Gln Tyr Gly Gly Cys Arg Gly Lys Lys Asn Asn Phe Lys Arg
1               5                   10                  15

Ala Lys Tyr

<210> SEQ ID NO 11
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+5)

<400> SEQUENCE: 11

Thr Phe Phe Tyr Gly Gly Cys Leu Gly Lys Arg Asn Asn Phe Lys Arg
1               5                   10                  15

Ala Lys Tyr

<210> SEQ ID NO 12
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+5)

<400> SEQUENCE: 12

Thr Phe Phe Tyr Gly Gly Ser Leu Gly Lys Arg Asn Asn Phe Lys Arg
1               5                   10                  15

Ala Lys Tyr
```

```
<210> SEQ ID NO 13
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+5)

<400> SEQUENCE: 13

Pro Phe Phe Tyr Gly Gly Cys Gly Gly Lys Lys Asn Asn Phe Lys Arg
1               5                   10                  15

Ala Lys Tyr

<210> SEQ ID NO 14
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+5)

<400> SEQUENCE: 14

Thr Phe Phe Tyr Gly Gly Cys Arg Gly Lys Gly Asn Asn Tyr Lys Arg
1               5                   10                  15

Ala Lys Tyr

<210> SEQ ID NO 15
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+5)

<400> SEQUENCE: 15

Pro Phe Phe Tyr Gly Gly Cys Arg Gly Lys Arg Asn Asn Phe Leu Arg
1               5                   10                  15

Ala Lys Tyr

<210> SEQ ID NO 16
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+5)

<400> SEQUENCE: 16

Thr Phe Phe Tyr Gly Gly Cys Arg Gly Lys Arg Asn Asn Phe Lys Arg
1               5                   10                  15

Glu Lys Tyr

<210> SEQ ID NO 17
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+5)

<400> SEQUENCE: 17

Pro Phe Phe Tyr Gly Gly Cys Arg Ala Lys Lys Asn Asn Phe Lys Arg
1               5                   10                  15
```

Ala Lys Glu

<210> SEQ ID NO 18
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+5)

<400> SEQUENCE: 18

Thr Phe Phe Tyr Gly Gly Cys Arg Gly Lys Arg Asn Asn Phe Lys Arg
1               5                   10                  15

Ala Lys Asp

<210> SEQ ID NO 19
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+4)

<400> SEQUENCE: 19

Thr Phe Phe Tyr Gly Gly Cys Arg Ala Lys Arg Asn Asn Phe Asp Arg
1               5                   10                  15

Ala Lys Tyr

<210> SEQ ID NO 20
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+4)

<400> SEQUENCE: 20

Thr Phe Phe Tyr Gly Gly Cys Arg Gly Lys Lys Asn Asn Phe Lys Arg
1               5                   10                  15

Ala Glu Tyr

<210> SEQ ID NO 21
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+4)

<400> SEQUENCE: 21

Pro Phe Phe Tyr Gly Gly Cys Gly Ala Asn Arg Asn Asn Phe Lys Arg
1               5                   10                  15

Ala Lys Tyr

<210> SEQ ID NO 22
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+4)

<400> SEQUENCE: 22

Thr Phe Phe Tyr Gly Gly Cys Gly Gly Lys Lys Asn Asn Phe Lys Thr
1               5                   10                  15

Ala Lys Tyr

<210> SEQ ID NO 23
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+4)

<400> SEQUENCE: 23

Thr Phe Phe Tyr Gly Gly Cys Arg Gly Asn Arg Asn Asn Phe Leu Arg
1               5                   10                  15

Ala Lys Tyr

<210> SEQ ID NO 24
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+4)

<400> SEQUENCE: 24

Thr Phe Phe Tyr Gly Gly Cys Arg Gly Asn Arg Asn Asn Phe Lys Thr
1               5                   10                  15

Ala Lys Tyr

<210> SEQ ID NO 25
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+4)

<400> SEQUENCE: 25

Thr Phe Phe Tyr Gly Gly Ser Arg Gly Asn Arg Asn Asn Phe Lys Thr
1               5                   10                  15

Ala Lys Tyr

<210> SEQ ID NO 26
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+3)

<400> SEQUENCE: 26

Thr Phe Phe Tyr Gly Gly Cys Leu Gly Asn Gly Asn Asn Phe Lys Arg
1               5                   10                  15

Ala Lys Tyr

<210> SEQ ID NO 27
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+3)

<400> SEQUENCE: 27

Thr Phe Phe Tyr Gly Gly Cys Leu Gly Asn Arg Asn Asn Phe Leu Arg

Ala Lys Tyr

<210> SEQ ID NO 28
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+3)

<400> SEQUENCE: 28

Thr Phe Phe Tyr Gly Gly Cys Leu Gly Asn Arg Asn Asn Phe Lys Thr
1               5                   10                  15

Ala Lys Tyr

<210> SEQ ID NO 29
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+3)

<400> SEQUENCE: 29

Thr Phe Phe Tyr Gly Gly Cys Arg Gly Asn Gly Asn Asn Phe Lys Ser
1               5                   10                  15

Ala Lys Tyr

<210> SEQ ID NO 30
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+3)

<400> SEQUENCE: 30

Thr Phe Phe Tyr Gly Gly Cys Arg Gly Lys Lys Asn Asn Phe Asp Arg
1               5                   10                  15

Glu Lys Tyr

<210> SEQ ID NO 31
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+3)

<400> SEQUENCE: 31

Thr Phe Phe Tyr Gly Gly Cys Arg Gly Lys Arg Asn Asn Phe Leu Arg
1               5                   10                  15

Glu Lys Glu

<210> SEQ ID NO 32
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+3)

<400> SEQUENCE: 32

```
Thr Phe Phe Tyr Gly Gly Cys Arg Gly Lys Gly Asn Asn Phe Asp Arg
1               5                   10                  15

Ala Lys Tyr
```

<210> SEQ ID NO 33
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+3)

<400> SEQUENCE: 33

```
Thr Phe Phe Tyr Gly Gly Ser Arg Gly Lys Gly Asn Asn Phe Asp Arg
1               5                   10                  15

Ala Lys Tyr
```

<210> SEQ ID NO 34
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+2)

<400> SEQUENCE: 34

```
Thr Phe Phe Tyr Gly Gly Cys Arg Gly Asn Gly Asn Asn Phe Val Thr
1               5                   10                  15

Ala Lys Tyr
```

<210> SEQ ID NO 35
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+2)

<400> SEQUENCE: 35

```
Pro Phe Phe Tyr Gly Gly Cys Gly Gly Lys Gly Asn Asn Tyr Val Thr
1               5                   10                  15

Ala Lys Tyr
```

<210> SEQ ID NO 36
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+2)

<400> SEQUENCE: 36

```
Thr Phe Phe Tyr Gly Gly Cys Leu Gly Lys Gly Asn Asn Phe Leu Thr
1               5                   10                  15

Ala Lys Tyr
```

<210> SEQ ID NO 37
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+2)

<400> SEQUENCE: 37

```
Ser Phe Phe Tyr Gly Gly Cys Leu Gly Asn Lys Asn Phe Leu Thr
1               5                   10                  15

Ala Lys Tyr

<210> SEQ ID NO 38
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+2) HUMAN

<400> SEQUENCE: 38

Thr Phe Phe Tyr Gly Gly Cys Gly Gly Asn Lys Asn Phe Val Arg
1               5                   10                  15

Glu Lys Tyr

<210> SEQ ID NO 39
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+2) HUMAN

<400> SEQUENCE: 39

Thr Phe Phe Tyr Gly Gly Cys Met Gly Asn Lys Asn Phe Val Arg
1               5                   10                  15

Glu Lys Tyr

<210> SEQ ID NO 40
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+2) HUMAN

<400> SEQUENCE: 40

Thr Phe Phe Tyr Gly Gly Ser Met Gly Asn Lys Asn Phe Val Arg
1               5                   10                  15

Glu Lys Tyr

<210> SEQ ID NO 41
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+2) HUMAN

<400> SEQUENCE: 41

Pro Phe Phe Tyr Gly Gly Cys Leu Gly Asn Arg Asn Asn Tyr Val Arg
1               5                   10                  15

Glu Lys Tyr

<210> SEQ ID NO 42
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+2) HUMAN
```

```
<400> SEQUENCE: 42

Thr Phe Phe Tyr Gly Gly Cys Leu Gly Asn Arg Asn Asn Phe Val Arg
1               5                   10                  15

Glu Lys Tyr

<210> SEQ ID NO 43
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+2) HUMAN

<400> SEQUENCE: 43

Thr Phe Phe Tyr Gly Gly Cys Leu Gly Asn Lys Asn Asn Tyr Val Arg
1               5                   10                  15

Glu Lys Tyr

<210> SEQ ID NO 44
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+1)

<400> SEQUENCE: 44

Thr Phe Phe Tyr Gly Gly Cys Gly Gly Asn Gly Asn Asn Phe Leu Thr
1               5                   10                  15

Ala Lys Tyr

<210> SEQ ID NO 45
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+1)

<400> SEQUENCE: 45

Thr Phe Phe Tyr Gly Gly Cys Arg Gly Asn Arg Asn Asn Phe Leu Thr
1               5                   10                  15

Ala Glu Tyr

<210> SEQ ID NO 46
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+1)

<400> SEQUENCE: 46

Thr Phe Phe Tyr Gly Gly Cys Arg Gly Asn Gly Asn Asn Phe Lys Ser
1               5                   10                  15

Ala Glu Tyr

<210> SEQ ID NO 47
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+1)
```

```
<400> SEQUENCE: 47

Pro Phe Phe Tyr Gly Gly Cys Leu Gly Asn Lys Asn Asn Phe Lys Thr
1               5                   10                  15

Ala Glu Tyr

<210> SEQ ID NO 48
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+1)

<400> SEQUENCE: 48

Thr Phe Phe Tyr Gly Gly Cys Arg Gly Asn Arg Asn Asn Phe Lys Thr
1               5                   10                  15

Glu Glu Tyr

<210> SEQ ID NO 49
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+1)

<400> SEQUENCE: 49

Thr Phe Phe Tyr Gly Gly Cys Arg Gly Lys Arg Asn Asn Phe Lys Thr
1               5                   10                  15

Glu Glu Asp

<210> SEQ ID NO 50
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+1) HUMAN

<400> SEQUENCE: 50

Pro Phe Phe Tyr Gly Gly Cys Gly Gly Asn Gly Asn Asn Phe Val Arg
1               5                   10                  15

Glu Lys Tyr

<210> SEQ ID NO 51
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+1) HUMAN

<400> SEQUENCE: 51

Ser Phe Phe Tyr Gly Gly Cys Met Gly Asn Gly Asn Asn Phe Val Arg
1               5                   10                  15

Glu Lys Tyr

<210> SEQ ID NO 52
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
```

Peptides CHARGE (+1) HUMAN

<400> SEQUENCE: 52

Pro Phe Phe Tyr Gly Gly Cys Gly Gly Asn Gly Asn Asn Phe Leu Arg
1               5                   10                  15

Glu Lys Tyr

<210> SEQ ID NO 53
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+1) HUMAN

<400> SEQUENCE: 53

Thr Phe Phe Tyr Gly Gly Cys Leu Gly Asn Gly Asn Asn Phe Val Arg
1               5                   10                  15

Glu Lys Tyr

<210> SEQ ID NO 54
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+1) HUMAN

<400> SEQUENCE: 54

Ser Phe Phe Tyr Gly Gly Cys Leu Gly Asn Gly Asn Asn Tyr Leu Arg
1               5                   10                  15

Glu Lys Tyr

<210> SEQ ID NO 55
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+1) HUMAN

<400> SEQUENCE: 55

Thr Phe Phe Tyr Gly Gly Ser Leu Gly Asn Gly Asn Asn Phe Val Arg
1               5                   10                  15

Glu Lys Tyr

<210> SEQ ID NO 56
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+0)

<400> SEQUENCE: 56

Thr Phe Phe Tyr Gly Gly Cys Arg Gly Asn Gly Asn Asn Phe Val Thr
1               5                   10                  15

Ala Glu Tyr

<210> SEQ ID NO 57
<211> LENGTH: 19
<212> TYPE: PRT
<213> ORGANISM: Artificial Sequence
<220> FEATURE:

-continued

```
<223> OTHER INFORMATION: A peptide similar to aprotinine and Angiopep-1:
      Peptides CHARGE (+0)

<400> SEQUENCE: 57

Thr Phe Phe Tyr Gly Gly Cys Leu Gly Lys Gly Asn Asn Phe Val Ser
1               5                   10                  15

Ala Glu Tyr

<210> SEQ ID NO 58
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+0)

<400> SEQUENCE: 58

Thr Phe Phe Tyr Gly Gly Cys Leu Gly Asn Arg Asn Asn Phe Asp Arg
1               5                   10                  15

Ala Glu Tyr

<210> SEQ ID NO 59
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+0) HUMAN

<400> SEQUENCE: 59

Thr Phe Phe Tyr Gly Gly Cys Leu Gly Asn Arg Asn Asn Phe Leu Arg
1               5                   10                  15

Glu Glu Tyr

<210> SEQ ID NO 60
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+0) HUMAN

<400> SEQUENCE: 60

Thr Phe Phe Tyr Gly Gly Cys Leu Gly Asn Lys Asn Asn Tyr Leu Arg
1               5                   10                  15

Glu Glu Tyr

<210> SEQ ID NO 61
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Peptides CHARGE (+0) HUMAN

<400> SEQUENCE: 61

Pro Phe Phe Tyr Gly Gly Cys Gly Gly Asn Arg Asn Asn Tyr Leu Arg
1               5                   10                  15

Glu Glu Tyr

<210> SEQ ID NO 62
<211> LENGTH: 19
<212> TYPE: PRT
<213> ORGANISM: Artificial Sequence
```

```
<220> FEATURE:
<223> OTHER INFORMATION: A peptide similar to aprotinine and Angiopep-1:
      Peptides CHARGE (+0) HUMAN

<400> SEQUENCE: 62

Pro Phe Phe Tyr Gly Gly Ser Gly Gly Asn Arg Asn Asn Tyr Leu Arg
1               5                   10                  15

Glu Glu Tyr

<210> SEQ ID NO 63
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Aprotinin M-term

<400> SEQUENCE: 63

Met Arg Pro Asp Phe Cys Leu Glu Pro Pro Tyr Thr Gly Pro Cys Val
1               5                   10                  15

Ala Arg Ile

<210> SEQ ID NO 64
<211> LENGTH: 21
<212> TYPE: PRT
<213> ORGANISM: Artificial Sequence
<220> FEATURE:
<223> OTHER INFORMATION: A peptide similar to aprotinine and Angiopep-1:
      Aprotinin M-term (1 helix alpha, A-term)

<400> SEQUENCE: 64

Ala Arg Ile Ile Arg Tyr Phe Tyr Asn Ala Lys Ala Gly Leu Cys Gln
1               5                   10                  15

Thr Phe Val Tyr Gly
            20

<210> SEQ ID NO 65
<211> LENGTH: 22
<212> TYPE: PRT
<213> ORGANISM: Artificial Sequence
<220> FEATURE:
<223> OTHER INFORMATION: A peptide similar to aprotinine and Angiopep-1:
      Aprotinin M-term (2 beta sheets, Y-term)

<400> SEQUENCE: 65

Tyr Gly Gly Cys Arg Ala Lys Arg Asn Asn Tyr Lys Ser Ala Glu Asp
1               5                   10                  15

Cys Met Arg Thr Cys Gly
            20

<210> SEQ ID NO 66
<211> LENGTH: 22
<212> TYPE: PRT
<213> ORGANISM: Artificial Sequence
<220> FEATURE:
<223> OTHER INFORMATION: A peptide similar to aprotinine and Angiopep-1:
      Aprotinin M-term (1 alpha, 1 beta)

<400> SEQUENCE: 66

Pro Asp Phe Cys Leu Glu Pro Pro Tyr Thr Gly Pro Cys Val Ala Arg
1               5                   10                  15

Ile Ile Arg Tyr Phe Tyr
            20
```

<210> SEQ ID NO 67
<211> LENGTH: 19
<212> TYPE: PRT
<213> ORGANISM: Artificial Sequence
<220> FEATURE:
<223> OTHER INFORMATION: A peptide similar to aprotinine and Angiopep-1: AngioPep-1
<220> FEATURE:
<221> NAME/KEY: MISC_FEATURE
<223> OTHER INFORMATION: may be amidated

<400> SEQUENCE: 67

Thr Phe Phe Tyr Gly Gly Cys Arg Gly Lys Arg Asn Asn Phe Lys Thr
1               5                   10                  15

Glu Glu Tyr

<210> SEQ ID NO 68
<211> LENGTH: 19
<212> TYPE: PRT
<213> ORGANISM: Artificial Sequence
<220> FEATURE:
<223> OTHER INFORMATION: A peptide similar to aprotinine and Angiopep-1: AngioPEP1 (Lysine)

<400> SEQUENCE: 68

Lys Phe Phe Tyr Gly Gly Cys Arg Gly Lys Arg Asn Asn Phe Lys Thr
1               5                   10                  15

Glu Glu Tyr

<210> SEQ ID NO 69
<211> LENGTH: 19
<212> TYPE: PRT
<213> ORGANISM: Artificial Sequence
<220> FEATURE:
<223> OTHER INFORMATION: A peptide similar to aprotinine and Angiopep-1: AngioPEP1 (4Y)

<400> SEQUENCE: 69

Thr Phe Tyr Tyr Gly Gly Cys Arg Gly Lys Arg Asn Asn Tyr Lys Thr
1               5                   10                  15

Glu Glu Tyr

<210> SEQ ID NO 70
<211> LENGTH: 19
<212> TYPE: PRT
<213> ORGANISM: Artificial Sequence
<220> FEATURE:
<223> OTHER INFORMATION: A peptide similar to aprotinine and Angiopep-1: cys bridge

<400> SEQUENCE: 70

Thr Phe Phe Tyr Gly Gly Ser Arg Gly Lys Arg Asn Asn Phe Lys Thr
1               5                   10                  15

Glu Glu Tyr

<210> SEQ ID NO 71
<211> LENGTH: 20
<212> TYPE: PRT
<213> ORGANISM: Artificial Sequence
<220> FEATURE:
<223> OTHER INFORMATION: A peptide similar to aprotinine and Angiopep-1: cys-Nterminal

<400> SEQUENCE: 71

Cys Thr Phe Phe Tyr Gly Cys Cys Arg Gly Lys Arg Asn Asn Phe Lys
1               5                   10                  15

Thr Glu Glu Tyr
            20

<210> SEQ ID NO 72
<211> LENGTH: 20
<212> TYPE: PRT
<213> ORGANISM: Artificial Sequence
<220> FEATURE:
<223> OTHER INFORMATION: A peptide similar to aprotinine and Angiopep-1:
      cys-Cterminal

<400> SEQUENCE: 72

Thr Phe Phe Tyr Gly Gly Cys Arg Gly Lys Arg Asn Asn Phe Lys Thr
1               5                   10                  15

Glu Glu Tyr Cys
            20

<210> SEQ ID NO 73
<211> LENGTH: 20
<212> TYPE: PRT
<213> ORGANISM: Artificial Sequence
<220> FEATURE:
<223> OTHER INFORMATION: A peptide similar to aprotinine and Angiopep-1:
      cys-Nterminal

<400> SEQUENCE: 73

Cys Thr Phe Phe Tyr Gly Ser Cys Arg Gly Lys Arg Asn Asn Phe Lys
1               5                   10                  15

Thr Glu Glu Tyr
            20

<210> SEQ ID NO 74
<211> LENGTH: 20
<212> TYPE: PRT
<213> ORGANISM: Artificial Sequence
<220> FEATURE:
<223> OTHER INFORMATION: A peptide similar to aprotinine and Angiopep-1:
      cys-Cterminal

<400> SEQUENCE: 74

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 75
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      pro

<400> SEQUENCE: 75

Pro Phe Phe Tyr Gly Gly Cys Arg Gly Lys Arg Asn Asn Phe Lys Thr
1               5                   10                  15

Glu Glu Tyr

<210> SEQ ID NO 76
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      charge (+3)

```
<220> FEATURE:
<221> NAME/KEY: MISC_FEATURE
<223> OTHER INFORMATION: may be amidated

<400> SEQUENCE: 76

Thr Phe Phe Tyr Gly Gly Cys Arg Gly Lys Arg Asn Asn Phe Lys Thr
1               5                   10                  15

Lys Glu Tyr

<210> SEQ ID NO 77
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      charge (+3)-cys

<400> SEQUENCE: 77

Thr Phe Phe Tyr Gly Gly Lys Arg Gly Lys Arg Asn Asn Phe Lys Thr
1               5                   10                  15

Glu Glu Tyr

<210> SEQ ID NO 78
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      charge (+4)

<400> SEQUENCE: 78

Thr Phe Phe Tyr Gly Gly Cys Arg Gly Lys Arg Asn Asn Phe Lys Thr
1               5                   10                  15

Lys Arg Tyr

<210> SEQ ID NO 79
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      charge (+4)-cys

<400> SEQUENCE: 79

Thr Phe Phe Tyr Gly Gly Lys Arg Gly Lys Arg Asn Asn Phe Lys Thr
1               5                   10                  15

Ala Glu Tyr

<210> SEQ ID NO 80
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      charge (+5)

<400> SEQUENCE: 80

Thr Phe Phe Tyr Gly Gly Lys Arg Gly Lys Arg Asn Asn Phe Lys Thr
1               5                   10                  15

Ala Gly Tyr

<210> SEQ ID NO 81
<211> LENGTH: 19
<212> TYPE: PRT
```

-continued

```
<213> ORGANISM: Artificial Sequence
<220> FEATURE:
<223> OTHER INFORMATION: A peptide similar to aprotinine and Angiopep-1:
      charge (+6)

<400> SEQUENCE: 81

Thr Phe Phe Tyr Gly Gly Lys Arg Gly Lys Arg Asn Asn Phe Lys Arg
1               5                   10                  15

Glu Lys Tyr

<210> SEQ ID NO 82
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      charge (+7)

<400> SEQUENCE: 82

Thr Phe Phe Tyr Gly Gly Lys Arg Gly Lys Arg Asn Asn Phe Lys Arg
1               5                   10                  15

Ala Lys Tyr

<210> SEQ ID NO 83
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      charge (0)

<400> SEQUENCE: 83

Thr Phe Phe Tyr Gly Gly Cys Leu Gly Asn Arg Asn Asn Phe Lys Thr
1               5                   10                  15

Glu Glu Tyr

<210> SEQ ID NO 84
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      permut cys(-)

<400> SEQUENCE: 84

Thr Phe Phe Tyr Gly Cys Gly Arg Gly Lys Arg Asn Asn Phe Lys Thr
1               5                   10                  15

Glu Glu Tyr

<210> SEQ ID NO 85
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      permut cys(+)

<400> SEQUENCE: 85

Thr Phe Phe Tyr Gly Gly Arg Cys Gly Lys Arg Asn Asn Phe Lys Thr
1               5                   10                  15

Glu Glu Tyr

<210> SEQ ID NO 86
<211> LENGTH: 19
```

```
<212> TYPE: PRT
<213> ORGANISM: Artificial Sequence
<220> FEATURE:
<223> OTHER INFORMATION: A peptide similar to aprotinine and Angiopep-1:
      charge(-4)

<400> SEQUENCE: 86

Thr Phe Phe Tyr Gly Gly Cys Leu Gly Asn Gly Asn Asn Phe Asp Thr
1               5                   10                  15

Glu Glu Glu

<210> SEQ ID NO 87
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Q instead of F

<400> SEQUENCE: 87

Thr Phe Gln Tyr Gly Gly Cys Arg Gly Lys Arg Asn Asn Phe Lys Thr
1               5                   10                  15

Glu Glu Tyr

<210> SEQ ID NO 88
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      ANGIOPEP scramble

<400> SEQUENCE: 88

Tyr Asn Lys Glu Phe Gly Thr Phe Asn Thr Lys Gly Cys Glu Arg Gly
1               5                   10                  15

Tyr Arg Phe

<210> SEQ ID NO 89
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      TFPI (similar domain)

<400> SEQUENCE: 89

Arg Phe Lys Tyr Gly Gly Cys Leu Gly Asn Met Asn Asn Phe Glu Thr
1               5                   10                  15

Leu Glu Glu

<210> SEQ ID NO 90
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Charge+5 (HUMAN)

<400> SEQUENCE: 90

Arg Phe Lys Tyr Gly Gly Cys Leu Gly Asn Lys Asn Asn Phe Leu Arg
1               5                   10                  15

Leu Lys Tyr

<210> SEQ ID NO 91
```

```
<211> LENGTH: 19
<212> TYPE: PRT
<213> ORGANISM: Artificial Sequence
<220> FEATURE:
<223> OTHER INFORMATION: A peptide similar to aprotinine and Angiopep-1:
      Charge+5 (HUMAN)
<220> FEATURE:
<221> NAME/KEY: MISC_FEATURE
<223> OTHER INFORMATION: may be amidated

<400> SEQUENCE: 91

Arg Phe Lys Tyr Gly Gly Cys Leu Gly Asn Lys Asn Asn Tyr Leu Arg
1               5                   10                  15

Leu Lys Tyr

<210> SEQ ID NO 92
<211> LENGTH: 22
<212> TYPE: PRT
<213> ORGANISM: Artificial Sequence
<220> FEATURE:
<223> OTHER INFORMATION: A peptide similar to aprotinine and Angiopep-1:
      TFPI (c-terminal) (2Y)

<400> SEQUENCE: 92

Lys Thr Lys Arg Lys Arg Lys Lys Gln Arg Val Lys Ile Ala Tyr Glu
1               5                   10                  15

Glu Ile Phe Lys Asn Tyr
            20

<210> SEQ ID NO 93
<211> LENGTH: 15
<212> TYPE: PRT
<213> ORGANISM: Artificial Sequence
<220> FEATURE:
<223> OTHER INFORMATION: A peptide similar to aprotinine and Angiopep-1:
      TFPI (c-terminal tronque)

<400> SEQUENCE: 93

Lys Thr Lys Arg Lys Arg Lys Lys Gln Arg Val Lys Ile Ala Tyr
1               5                   10                  15

<210> SEQ ID NO 94
<211> LENGTH: 17
<212> TYPE: PRT
<213> ORGANISM: SynB1
<220> FEATURE:
<223> OTHER INFORMATION: A peptide similar to aprotinine and Angiopep-1:
      polypeptide

<400> SEQUENCE: 94

Arg Gly Gly Arg Leu Ser Tyr Ser Arg Arg Phe Ser Thr Ser Thr Gly
1               5                   10                  15

Arg

<210> SEQ ID NO 95
<211> LENGTH: 10
<212> TYPE: PRT
<213> ORGANISM: Artificial Sequence
<220> FEATURE:
<223> OTHER INFORMATION: A peptide similar to aprotinine and Angiopep-1:
      SynB3

<400> SEQUENCE: 95

Arg Arg Leu Ser Tyr Ser Arg Arg Arg Phe
1               5                   10
```

```
<210> SEQ ID NO 96
<211> LENGTH: 16
<212> TYPE: PRT
<213> ORGANISM: Artificial Sequence
<220> FEATURE:
<223> OTHER INFORMATION: A peptide similar to aprotinine and Angiopep-1:
      Penetratin (pAntp43-68)

<400> SEQUENCE: 96

Arg Gln Ile Lys Ile Trp Phe Gln Asn Arg Arg Met Lys Trp Lys Lys
1               5                   10                  15

<210> SEQ ID NO 97
<211> LENGTH: 19
<212> TYPE: PRT
<213> ORGANISM: Artificial Sequence
<220> FEATURE:
<223> OTHER INFORMATION: Angiopep-2

<400> SEQUENCE: 97

Thr Phe Phe Tyr Gly Gly Ser Arg Gly Lys Arg Asn Asn Phe Lys Thr
1               5                   10                  15

Glu Glu Tyr

<210> SEQ ID NO 98
<211> LENGTH: 59
<212> TYPE: PRT
<213> ORGANISM: Artificial Sequence
<220> FEATURE:
<223> OTHER INFORMATION: Aprotinin

<400> SEQUENCE: 98

Met Arg Pro Asp Phe Cys Leu Glu Pro Pro Tyr Thr Gly Pro Cys Val
1               5                   10                  15

Ala Arg Ile Ile Arg Tyr Phe Tyr Asn Ala Lys Ala Gly Leu Cys Gln
            20                  25                  30

Thr Phe Val Tyr Gly Gly Cys Arg Ala Lys Arg Asn Asn Phe Lys Ser
        35                  40                  45

Ala Glu Asp Cys Met Arg Thr Cys Gly Gly Ala
    50                  55

<210> SEQ ID NO 99
<211> LENGTH: 19
<212> TYPE: PRT
<213> ORGANISM: Artificial Sequence
<220> FEATURE:
<223> OTHER INFORMATION: A biologically active analogue of Aprot-Synth
      peptide

<400> SEQUENCE: 99

Thr Phe Phe Tyr Gly Gly Cys Arg Gly Lys Arg Asn Asn Phe Lys Thr
1               5                   10                  15

Lys Glu Tyr

<210> SEQ ID NO 100
<211> LENGTH: 19
<212> TYPE: PRT
<213> ORGANISM: Artificial Sequence
<220> FEATURE:
<223> OTHER INFORMATION: A biologically active analogue of Aprot-Synth
      peptide

<400> SEQUENCE: 100

Arg Phe Lys Tyr Gly Gly Cys Leu Gly Asn Lys Asn Asn Tyr Leu Arg
1               5                   10                  15
```

Leu Lys Tyr

<210> SEQ ID NO 101
<211> LENGTH: 19
<212> TYPE: PRT
<213> ORGANISM: Artificial Sequence
<220> FEATURE:
<223> OTHER INFORMATION: A biologically active analogue of Aprot-Synth
      peptide

<400> SEQUENCE: 101

Thr Phe Phe Tyr Gly Gly Cys Arg Ala Lys Arg Asn Asn Phe Lys Arg
1               5                   10                  15

Ala Lys Tyr

<210> SEQ ID NO 102
<211> LENGTH: 35
<212> TYPE: PRT
<213> ORGANISM: Artificial Sequence
<220> FEATURE:
<223> OTHER INFORMATION: An aprotinin analog
<300> PUBLICATION INFORMATION:
<310> PATENT DOCUMENT NUMBER: US 5,807,980
<311> PATENT FILING DATE: 1993-07-01
<312> PUBLICATION DATE: 1998-09-15

<400> SEQUENCE: 102

Asn Ala Lys Ala Gly Leu Cys Gln Thr Phe Val Tyr Gly Gly Cys Leu
1               5                   10                  15

Ala Lys Arg Asn Asn Phe Glu Ser Ala Glu Asp Cys Met Arg Thr Cys
                20                  25                  30

Gly Gly Ala
        35

<210> SEQ ID NO 103
<211> LENGTH: 24
<212> TYPE: PRT
<213> ORGANISM: Artificial Sequence
<220> FEATURE:
<223> OTHER INFORMATION: A Serine protease inhibitor
<300> PUBLICATION INFORMATION:
<310> PATENT DOCUMENT NUMBER: US 5,780,265
<311> PATENT FILING DATE: 1995-07-05
<312> PUBLICATION DATE: 1998-07-14

<400> SEQUENCE: 103

Tyr Gly Gly Cys Arg Ala Lys Arg Asn Asn Phe Lys Ser Ala Glu Asp
1               5                   10                  15

Cys Met Arg Thr Cys Gly Gly Ala
                20

<210> SEQ ID NO 104
<211> LENGTH: 22
<212> TYPE: PRT
<213> ORGANISM: Artificial Sequence
<220> FEATURE:
<223> OTHER INFORMATION: An aprotinin analog
<300> PUBLICATION INFORMATION:
<310> PATENT DOCUMENT NUMBER: WO04/060403
<311> PATENT FILING DATE: 2004-01-05
<312> PUBLICATION DATE: 2004-06-22

<400> SEQUENCE: 104

Gly Leu Cys Gln Thr Phe Val Tyr Gly Gly Cys Arg Ala Lys Arg Asn
1               5                   10                  15

```
Asn Phe Lys Ser Ala Glu
            20

<210> SEQ ID NO 105
<211> LENGTH: 20
<212> TYPE: PRT
<213> ORGANISM: Artificial Sequence
<220> FEATURE:
<223> OTHER INFORMATION: A peptide with similar sequence to Angiopep-1
<300> PUBLICATION INFORMATION:
<310> PATENT DOCUMENT NUMBER: US 5,118,668
<311> PATENT FILING DATE: 1988-07-20
<312> PUBLICATION DATE: 1992-06-02

<400> SEQUENCE: 105

Leu Cys Gln Thr Phe Val Tyr Gly Gly Cys Glu Ala Lys Arg Asn Asn
1               5                   10                  15

Phe Lys Ser Ala
            20

<210> SEQ ID NO 106
<211> LENGTH: 180
<212> TYPE: DNA
<213> ORGANISM: Artificial Sequence
<220> FEATURE:
<223> OTHER INFORMATION: An exemplary nucleotide sequence encoding an
      aprotinin analogue
<300> PUBLICATION INFORMATION:
<308> DATABASE ACCESSION NUMBER: X04666
<309> DATABASE ENTRY DATE: 1993-09-13
<313> RELEVANT RESIDUES IN SEQ ID NO: (217)..(396)

<400> SEQUENCE: 106
atgagaccag atttctgcct cgagccgccg tacactgggc cctgcaaagc tcgtatcatc         60
cgttacttct acaatgcaaa ggcaggcctg tgtcagacct tcgtatacgg cggctgcaga        120
gctaagcgta acaacttcaa atccgcggaa gactgcatgc gtacttgcgg tggtgcttag        180
```